US012588943B2

(12) United States Patent
Deen et al.

(10) Patent No.: US 12,588,943 B2
(45) Date of Patent: Mar. 31, 2026

(54) ELECTRICALLY ENHANCED RETRIEVAL OF MATERIAL FROM VESSEL LUMENS

(71) Applicant: Covidien LP, Mansfield, MA (US)

(72) Inventors: Daniel Deen, Long Beach, CA (US); Ashok Nageswaran, Irvine, CA (US); Hoai Nguyen, Westminster, CA (US)

(73) Assignee: COVIDIEN LP, Mansfield, MA (US)

( * ) Notice: Subject to any disclaimer, the term of this patent is extended or adjusted under 35 U.S.C. 154(b) by 971 days.

(21) Appl. No.: 17/453,624

(22) Filed: Nov. 4, 2021

(65) Prior Publication Data

US 2022/0192739 A1 Jun. 23, 2022

Related U.S. Application Data

(60) Provisional application No. 63/199,352, filed on Dec. 21, 2020.

(51) Int. Cl.
*A61B 18/00* (2006.01)
*A61B 18/12* (2006.01)
*A61B 18/14* (2006.01)

(52) U.S. Cl.
CPC ...... *A61B 18/1492* (2013.01); *A61B 18/1206* (2013.01); *A61B 2018/00077* (2013.01); *A61B 2018/00083* (2013.01); *A61B 2018/00404* (2013.01); *A61B 2018/126* (2013.01)

(58) Field of Classification Search
CPC .......... A61B 17/3205; A61B 17/32053; A61B 17/32056; A61B 17/3207; A61B 17/221; A61B 2017/2212–2217; A61B 18/1492; A61B 2018/1495; A61B 2018/00404;

A61B 2018/0041; A61B 2018/00416; A61B 2018/00422; A61B 2018/00053; A61B 2018/00172; A61B 2018/00178
See application file for complete search history.

(56) References Cited

U.S. PATENT DOCUMENTS

| | | |
|---|---|---|
| 7,300,458 B2 | 11/2007 | Henkes et al. |
| 8,066,757 B2 | 11/2011 | Ferrera et al. |
| 8,940,003 B2 | 1/2015 | Slee et al. |
| 9,039,749 B2 | 5/2015 | Shrivastava et al. |

(Continued)

FOREIGN PATENT DOCUMENTS

EP 3815633 A1 5/2021

OTHER PUBLICATIONS

International Search Report and Written Opinion mailed May 11, 2022; International Application No. PCT/US2021/060272; 21 pages.

*Primary Examiner* — Linda C Dvorak
*Assistant Examiner* — Davina E. Lee
(74) *Attorney, Agent, or Firm* — Fortem IP LLP

(57) ABSTRACT

Retrieval of material from vessel lumens can be improved by electrically enhancing attachment of the material to the thrombectomy system. The system can include a manipulation member configured to be electrically coupled to an extracorporeal power supply and an interventional element configured to be mechanically and electrically coupled to the manipulation member via a joining element. A locking element can be positioned within the joining element to facilitate securing the interventional element to the joining element. In some embodiments, the system includes a control member configured to be coupled to a second terminal of the extracorporeal power supply and positioned within a lumen of the locking element.

25 Claims, 14 Drawing Sheets

(56) References Cited

U.S. PATENT DOCUMENTS

| 2007/0186933 | A1* | 8/2007 | Domingo | A61B 17/12104 |
| | | | | 606/205 |
| 2007/0299459 | A1* | 12/2007 | Way | A61B 17/3421 |
| | | | | 606/185 |
| 2014/0194911 | A1 | 7/2014 | Johnson et al. | |
| 2018/0263650 | A1 | 9/2018 | Iwanami et al. | |
| 2018/0280128 | A1* | 10/2018 | Spenser | A61F 2/011 |
| 2019/0175200 | A1* | 6/2019 | Girdhar | A61B 17/22031 |
| 2020/0100804 | A1 | 4/2020 | Casey et al. | |
| 2020/0390458 | A1 | 12/2020 | Nguyen et al. | |

* cited by examiner

ELECTRICALLY ENHANCED RETRIEVAL OF MATERIAL FROM VESSEL LUMENS

CROSS-REFERENCE TO RELATED APPLICATION(S)

The present application claims the benefit of priority of U.S. Provisional Application No. 63/199,352, filed Dec. 21, 2020, which is incorporated by reference herein in its entirety.

TECHNICAL FIELD

The present technology relates to relates generally to devices, systems, and methods for removing obstructions from body lumens. Some embodiments of the present technology relate to devices and methods for removal of clot material from blood vessels.

BACKGROUND

Many medical procedures use medical device(s) to remove an obstruction (such as clot material) from a body lumen, vessel, or other organ. An inherent risk in such procedures is that mobilizing or otherwise disturbing the obstruction can potentially create further harm if the obstruction or a fragment thereof dislodges from the retrieval device. If all or a portion of the obstruction breaks free from the device and flows downstream, it is highly likely that the free material will become trapped in smaller and more tortuous anatomy. In many cases, the physician will no longer be able to use the same retrieval device to again remove the obstruction because the device may be too large and/or immobile to move the device to the site of the new obstruction.

Procedures for treating ischemic stroke by restoring flow within the cerebral vasculature are subject to the above concerns. The brain relies on its arteries and veins to supply oxygenated blood from the heart and lungs and to remove carbon dioxide and cellular waste from brain tissue. Blockages that interfere with this blood supply eventually cause the brain tissue to stop functioning. If the disruption in blood occurs for a sufficient amount of time, the continued lack of nutrients and oxygen causes irreversible cell death. Accordingly, it is desirable to provide immediate medical treatment of an ischemic stroke.

To access the cerebral vasculature, a physician typically advances a catheter from a remote part of the body (typically a leg) through the abdominal vasculature and into the cerebral region of the vasculature. Once within the cerebral vasculature, the physician deploys a device for retrieval of the obstruction causing the blockage. Concerns about dislodged obstructions or the migration of dislodged fragments increases the duration of the procedure at a time when restoration of blood flow is paramount. Furthermore, a physician might be unaware of one or more fragments that dislodge from the initial obstruction and cause blockage of smaller more distal vessels.

Many physicians currently perform thrombectomies (i.e. clot removal) with stents to resolve ischemic stroke. Typically, the physician deploys a stent into the clot in an attempt to push the clot to the side of the vessel and re-establish blood flow. Tissue plasminogen activator ("tPA") is often injected into the bloodstream through an intravenous line to break down a clot. However, it takes time for the tPA to reach the clot because the tPA must travel through the vasculature and only begins to break up the clot once it reaches the clot material. tPA is also often administered to supplement the effectiveness of the stent. Yet, if attempts at clot dissolution are ineffective or incomplete, the physician can attempt to remove the stent while it is expanded against or enmeshed within the clot. In doing so, the physician must effectively drag the clot through the vasculature, in a proximal direction, into a guide catheter located within vessels in the patient's neck (typically the carotid artery). While this procedure has been shown to be effective in the clinic and easy for the physician to perform, there remain some distinct disadvantages to using this approach.

For example, one disadvantage is that the stent may not sufficiently retain the clot as it pulls the clot to the catheter. In such a case, some or all of the clot might remain in the vasculature. Another risk is that, as the stent mobilizes the clot from the original blockage site, the clot might not adhere to the stent as the stent is withdrawn toward the catheter. This is a particular risk when passing through bifurcations and tortuous anatomy. Furthermore, blood flow can carry the clot (or fragments of the clot) into a branching vessel at a bifurcation. If the clot is successfully brought to the end of the guide catheter in the carotid artery, yet another risk is that the clot may be "stripped" or "sheared" from the stent as the stent enters the guide catheter.

In view of the above, there remains a need for improved devices and methods that can remove occlusions from body lumens and/or vessels.

SUMMARY

Mechanical thrombectomy (i.e., clot-grabbing and removal) has been effectively used for treatment of ischemic stroke. Although most clots can be retrieved in a single pass attempt, there are instances in which multiple attempts are needed to fully retrieve the clot and restore blood flow through the vessel. Additionally, there exist complications due to detachment of the clot from the interventional element during the retrieval process as the interventional element and clot traverse through tortuous intracranial vascular anatomy. For example, the detached clot or clot fragments can obstruct other arteries leading to secondary strokes. The failure modes that contribute to clot release during retrieval are: (a) boundary conditions at bifurcations; (b) changes in vessel diameter; and (c) vessel tortuosity, amongst others.

Certain blood components, such as platelets and coagulation proteins, display negative electrical charges. The treatment systems of the present technology provide an interventional element and a current generator configured to positively charge the interventional element during one or more stages of a thrombectomy procedure. For example, the current generator may apply a constant or pulsatile direct current (DC) to the interventional element. The positively charged interventional element attracts negatively charged blood components, thereby improving attachment of the thrombus to the interventional element and reducing the number of device passes or attempts necessary to fully retrieve the clot. In some aspects of the present technology, the treatment system includes an elongate manipulation member extending between the current generator and the interventional element. A positive (e.g., delivery) electrode may be integrated into the manipulation member and/or interventional element, and the treatment system further includes a return electrode that may be disposed at a number of different locations. For example, the return electrode can be a wire coupled to the manipulation member. Additionally or alternatively, a return electrode can take the form of a needle, a grounding pad, a conductive element carried by a one or more catheters of the treatment system, a separate guide wire, and/or any other suitable conductive element configured to complete an electrical circuit with the delivery electrode and the extracorporeally positioned current generator. When the interventional element is placed in the presence of blood (or any other electrolytic medium) and voltage is applied at the terminals of the current generator, current flows along the core member to the interventional element, through the blood, and to the return electrode, thereby positively charging at least a portion of the interventional element and adhering clot material thereto.

One approach to delivering current to an interventional element is to conduct current along an elongate manipulation member coupled to a proximal end of the interventional element at a connection. The connection can be configured to both mechanically and electrically couple the interventional element and the manipulation member. For example, the manipulation member can comprise a distally located joining element including an aperture extending therethrough. The interventional element can comprise a proximally located attachment portion configured to be inserted into the aperture of the joining element while positioned in a first orientation. The attachment portion can be configured to mechanically interlock with the joining element to prevent and/or limit motion of the interventional element relative to the joining element and to form an electrical connection between the interventional element and the joining element. For example, the attachment portion can be movable between the first orientation and a second orientation in which the attachment portion is mechanically interlocked with the joining element. In some cases, a locking element can be employed to limit motion of the attachment portion with respect to the joining element. The joining element can be electrically coupled to the manipulation member so that current can pass from the manipulation member to the interventional element via the joining element. In some embodiments, the return electrode comprises a core member configured to be positioned within a lumen of the manipulation member and the aperture of the joining element such that a proximal end of the core member extends proximally of the manipulation member and a distal end of the core member extends distally of the joining element. An electrically insulating material can be disposed between at least a portion of the core member and the joining element, the manipulation member, and/or the attachment portion.

Additional features and advantages of the present technology are described below, and in part will be apparent from the description, or may be learned by practice of the present technology. The advantages of the present technology will be realized and attained by the structure particularly pointed out in the written description and claims hereof as well as the appended drawings. The subject technology is illustrated, for example, according to various aspects described below. Various examples of aspects of the subject technology are described as numbered clauses (1, 2, 3, etc.) for convenience. These are provided as examples and do not limit the subject technology.

1. A medical device comprising:
an elongate manipulation member comprising a distally located joining element, the joining element including an aperture; and
an interventional element comprising a proximally located attachment portion, the attachment portion configured to extend through the aperture to mate with the joining element.
2. The medical device of Clause 1, further comprising a control member extending longitudinally through the aperture at a position radially adjacent the attachment portion, the control member retaining the interventional element in position with respect to the joining element.
3. The medical device of Clause 1 or Clause 2, wherein the elongate manipulation member comprises an elongate tubular member defining a lumen therethrough, and wherein the control member extends through the elongate tubular member lumen.
4. The medical device of any one of Clauses 1 to 3, wherein the control member is slidably disposed within the aperture.
5. The medical device of any one of Clauses 1 to 4, wherein the control member is affixed with respect to the joining element via an adhesive.
6. The medical device of any one of Clauses 1 to 5, wherein the aperture has a cross-sectional dimension that is greater along a first direction than along a second direction orthogonal to the first direction.
7. The medical device of any one of Clauses 1 to 6, wherein the attachment portion comprises a retention region and an engagement feature disposed proximal of the retention region.
8. The medical device of Clause 7, wherein the engagement feature has a greatest cross-sectional dimension that is larger than a greatest cross-sectional dimension of the retention region.
9. The medical device of Clause 7 or Clause 8, wherein the engagement feature comprises one or more flanges extending outwardly (e.g. laterally outwardly, circumferentially outwardly, or radially outwardly) with respect to the retention region.
10. The medical device of any one of Clauses 7 to 9, wherein the engagement feature has a greatest cross-sectional dimension that is greater than a first cross-sectional dimension of the aperture along a first axis, and less than a second cross-sectional dimension of the aperture along a second axis.
11. The medical device of Clause 10, wherein the second axis is orthogonal to the first axis.
12. The medical device of any one of Clauses 7 to 11, wherein the engagement feature is sized and configured to pass through the aperture in a first orientation but to not pass through the aperture in a second orientation.
13. The medical device of Clause 12, wherein the second orientation is rotated in a radial direction with respect to the first orientation.
14. The medical device of any one of Clauses 7 to 13, wherein the retention region has a greatest cross-sectional dimension that is less than a smallest cross-sectional dimension of the aperture.
15. The medical device of any one of Clauses 1 to 14, wherein the elongate manipulation member and interventional element are in electrical communication with one another via the joining element, such that current supplied to the elongate manipulation member passes to the interventional element.
16. The medical device of any one of Clauses 1 to 15, wherein the elongate manipulation member comprises a hypotube.
17. The medical device of any one of Clauses 1 to 16, wherein the control member comprises an electrically conductive wire having one or more insulated portions along a length of the control member.
18. The medical device of any one of Clauses 1 to 17, wherein the interventional element forms an electrode.

19. The medical device of any one of Clauses 1 to 18, further comprising at least one electrode coupled to the interventional element.

20. The medical device of Clause 18 or Clause 19, wherein the electrode has a surface formed of gold.

21. The medical device of Clause 20, wherein the surface is an outer surface of the electrode.

22. The medical device of any one of Clauses 1 to 21, wherein the control member forms an electrode.

23. The medical device of any one of Clauses 1 to 22, further comprising at least one electrode coupled to the control member.

24. The medical device of Clause 22 or Clause 23, wherein the electrode has a surface formed of gold.

25. The medical device of Clause 24, wherein the surface is an outer surface of the electrode.

26. The medical device of any one of Clauses 1 to 25, further comprising a first electrode formed by or coupled to the interventional element and a second electrode formed by or coupled to the control member, wherein the first and second electrodes are configured to be of opposite polarities.

27. The medical device of any one of Clauses 1 to 26, wherein the control member provides a first current path through the aperture of the joining element which is insulated from a second current path conducted by the joining element to the interventional element.

28. The medical device of any one of Clauses 1 to 27, wherein a filler material is disposed within the aperture of the joining element.

29. The medical device of Clause 28, wherein the filler material comprises solder, adhesive, or epoxy.

30. The medical device of any one of Clauses 1 to 29, further comprising a locking element configured to be positioned within the aperture of the joining element.

31. The medical device of Clause 30, wherein the aperture of the joining element comprises a first portion and a second portion, the second portion being radially adjacent to the first portion.

32. The medical device of Clause 31, wherein the locking element is configured to be positioned within the first portion of the aperture and the attachment portion is configured to be positioned within the second portion of the aperture.

33. The medical device of any one of Clauses 1 to 32, wherein the locking element has a lumen extending therein.

34. The medical device of Clause 33, wherein the control member is configured to extend longitudinally through the lumen of the locking element.

35. The medical device of any one of Clauses 1 to 34, wherein a cross-sectional shape of the locking element generally corresponds to a cross-sectional shape of at least a portion of the aperture of the joining element.

36. The medical device of any one of Clauses 1 to 35, wherein the locking element is generally tubular.

37. The medical device of any one of Clauses 1 to 36, wherein the locking element within the aperture of the joining element via an interference fit, a transition fit, or a clearance fit.

38. A medical device comprising:

a manipulation assembly having a distal portion configured to be intravascularly positioned within a blood vessel lumen, the manipulation assembly comprising:

an elongate tubular member, the tubular member having a proximal portion, a distal portion, and a lumen extending therein;

a control member extending through the lumen of the tubular member; and a joining element located at the distal portion of the elongate tubular member, the joining element having a proximal-facing surface, a distal-facing surface opposite the proximal-facing surface along a length of the joining element, a sidewall therebetween, and a lumen extending from the proximal-facing surface to the distal-facing surface of the joining element; and an interventional element comprising a proximally located attachment portion having a distal region, a proximal region, and a retention region therebetween, wherein the distal region comprises a first engagement feature protruding outwardly with respect to the retention region and the proximal region comprises a second engagement feature protruding outwardly with respect to the retention region, wherein the first engagement feature is configured to prevent and/or limit proximal translation of the interventional element relative to the joining element and the second engagement feature is configured to prevent and/or limit distal translation of the interventional element relative to the joining element.

39. The medical device of Clause 38, wherein the lumen comprises a first portion having a first cross-sectional shape and a second portion having a second cross-sectional shape, and wherein the second portion is radially adjacent to the first portion.

40. The medical device of Clause 39, wherein the manipulation assembly comprises a locking element having a cross-sectional shape corresponding, at least in part, to the first cross-sectional shape of the first portion of the lumen of the joining element.

41. The medical device of any one of Clauses 39 to 40, wherein the retention region is positioned within the second portion of the lumen of the joining element such that the first engagement feature is configured to prevent and/or limit proximal translation of the interventional element relative to the joining element and the second engagement feature is configured to prevent and/or limit distal translation of the interventional element relative to the joining element.

42. The medical device of Clause 40 or Clause 41, wherein the locking element is positioned within the first portion of the lumen of the joining element such that the locking element is configured to prevent and/or limits radial translation of the retention region within the lumen of the joining element.

43. The medical device of any one of Clauses 38 to 42 wherein the elongate tubular member is configured to be coupled to a first terminal of an extracorporeal power supply, and wherein the control member is configured to be coupled to a second terminal of the extracorporeal power supply.

44. The medical device of any one of Clauses 38 to 43, wherein the control member is configured to extend through the lumen of the joining element.

45. The medical device of Clause 43 or Clause 44, wherein, when the interventional element is in the presence of an electrolytic medium and voltage is supplied to the first and second electrical terminals, current flows from the interventional element to the electrolytic medium to the control member.

46. The medical device of any one of Clauses 38 to 45, further comprising an electrically insulating material disposed between at least a portion of the elongate tubular member and at least a portion of the control member.

47. The medical device of any one of Clauses 38 to 46, wherein the lumen of the joining element has a generally oblong cross-sectional shape.

48. The medical device of any one of Clauses 38 to 47, wherein the lumen of the joining element has a diameter less than a diameter of the lumen of the hypotube.

49. The medical device of any one of Clauses 38 to 48, wherein the proximal region of the attachment portion has a first width, the distal region of the attachment portion has a second width, and the retention region of the attachment portion has a third width less than the first width and the second width.

50. The medical device of any one of Clauses 38 to 49, wherein the retention region is positioned within the lumen of the joining element such that the first engagement feature abuts the distal-facing surface of the joining element and the second engagement feature abuts the proximal-facing surface of the joining element.

51. The medical device of any one of Clauses 38 to 50, wherein the interventional element is configured to be coupled to the manipulation assembly by positioning the distal and retention regions of the attachment portion of the interventional element within the lumen of the joining element while the attachment portion is positioned in a first orientation and rotating the attachment portion into a second orientation such that the first and second engagement features abut the distal-facing and proximal-facing surfaces, respectively, of the joining element.

52. The medical device of any one of Clauses 38 to 51, wherein the sidewall of the joining element is generally annular.

53. The medical device of Clause 52, wherein the joining element has an outer diameter substantially equivalent to an outer diameter of the elongate tubular member.

54. The medical device of any one of Clauses 38 to 53, wherein the joining element is coupled to the distal portion of the elongate tubular member via welding or adhesive.

55. The medical device of any one of Clauses 38 to 54, wherein the first engagement feature comprises a substantially planar proximal-facing surface configured to engage the joining element.

56. The medical device of any one of Clauses 38 to 55, wherein the second engagement feature comprises a substantially planar distal-facing surface configured to engage the joining element.

57. The medical device of any one of Clauses 38 to 56, wherein the attachment portion is radially outwardly biased, and wherein the joining element is configured to retain the attachment portion in a displaced state.

58. The medical device of any one of Clauses 38 to 57, wherein the first and second engagement features each protrude radially or laterally outwardly with respect to the retention region.

59. The medical device of any one of Clauses 38 to 58, wherein the interventional element forms an electrode.

60. The medical device of any one of Clauses 38 to 59, further comprising at least one electrode coupled to the interventional element.

61. The medical device of Clause 59 or Clause 60, wherein the electrode has a surface formed of gold.

62. The medical device of Clause 61, wherein the surface is an outer surface of the electrode.

63. The medical device of any one of Clauses 38 to 62, wherein the control member forms an electrode.

64. The medical device of any one of Clauses 38 to 63, further comprising at least one electrode coupled to the control member.

65. The medical device of Clause 63 or Clause 64, wherein the electrode has a surface formed of gold.

66. The medical device of Clause 65, wherein the surface is an outer surface of the electrode.

67. The medical device of any one of Clauses 38 to 66, further comprising a first electrode formed by or coupled to the interventional element and a second electrode formed by or coupled to the control member, wherein the first and second electrodes are configured to be of opposite polarities.

68. The medical device of any one of Clauses 38 to 67, wherein the control member provides a first current path through the aperture of the joining element which is insulated from a second current path conducted by the joining element to the interventional element.

69. The medical device of any one of Clauses 38 to 68, wherein a filler material is disposed within the aperture of the joining element.

70. The medical device of Clause 69, wherein the filler material comprises solder, adhesive, or epoxy.

71. The medical device of any one of Clauses 38 to Clause 70, wherein the control member does not extend through the lumen of the joining element.

72. A medical device comprising:
a manipulation assembly having a distal portion configured to be intravascularly positioned within a blood vessel lumen, the manipulation assembly comprising:
    a hypotube configured to be coupled to a first electrical terminal, the hypotube having a proximal portion, a distal portion, and a lumen extending therein;
    an elongate member configured to be coupled to a second electrical terminal, the elongate member extending through the lumen of the hypotube;
    an insulating layer disposed between at least a portion of the hypotube and at least a portion of the elongate member; and
    a joining element located at the distal portion of the hypotube, the joining element comprising a first end surface, a second end surface opposite the first end surface along a length of the joining element, an annular sidewall therebetween, and a lumen extending from the first end surface to the second end surface of the joining element; and
an interventional element comprising an attachment portion comprising a projection including a flange extending away from a longitudinal axis of the device,
wherein the projection is configured to be positioned within the lumen of the joining element such that the flange engages the joining element and prevents and/or limits movement of the interventional element with respect to the joining element.

73. The medical device of Clause 72, wherein the manipulation assembly comprises a tubular element positioned within the lumen of the joining element.

74. The medical device of Clause 73, wherein the projection is positioned within the lumen of the joining element at a position radially adjacent to the tubular element such that the tubular element prevents and/or limits radial movement of the interventional element with respect to the joining element and the flange engages the joining element and prevents and/or limits longitudinal movement of the interventional element with respect to the joining element.

75. The medical device of any one of Clauses 72 to 74, wherein the flange is a first flange, the projection including a second flange extending away from a longitudinal axis of the device.

76. The medical device of Clause 75, wherein the first flange is configured to engage the first end surface of the joining element and the second flange is configured to engage the second end surface of the joining element.

77. The medical device of Clause 75 or Clause 76, wherein the first flange is configured to limit distal movement of the interventional element with respect to the joining element.

78. The medical device of any one of Clauses 75 to 77, wherein the second flange is configured to limit proximal movement of the interventional element with respect to the joining element.

79. The medical device of any one of Clauses 72 to 78, wherein the interventional element is movable between a first orientation in which the attachment portion is configured to be slidably received within the lumen of the joining element and a second orientation in which the flange engages the joining element.

80. The medical device of any one or Clauses 72 to 79, wherein the flange extends laterally away from a longitudinal axis of the device.

81. The medical device of any one of Clauses 72 to 80, wherein the interventional element forms an electrode.

82. The medical device of any one of Clauses 72 to 81, further comprising at least one electrode coupled to the interventional element.

83. The medical device of Clause 81 or Clause 82, wherein the electrode has a surface formed of gold.

84. The medical device of Clause 83, wherein the surface is an outer surface of the electrode.

85. The medical device of any one of Clauses 72 to 84, wherein the elongate member forms an electrode.

86. The medical device of any one of Clauses 72 to 85, further comprising at least one electrode coupled to the elongate member.

87. The medical device of Clause 85 or Clause 86, wherein the electrode has a surface formed of gold.

88. The medical device of Clause 87, wherein the surface is an outer surface of the electrode.

89. The medical device of any one of Clauses 72 to 88, further comprising a first electrode formed by or coupled to the interventional element and a second electrode formed by or coupled to the elongate member, wherein the first and second electrodes are configured to be of opposite polarities.

90. The medical device of any one of Clauses 72 to 89, wherein the elongate member provides a first current path through the aperture of the joining element which is insulated from a second current path conducted by the joining element to the interventional element.

91. The medical device of any one of Clauses 72 to 90, wherein a filler material is disposed within the aperture of the joining element.

92. The medical device of Clause 91, wherein the filler material comprises solder, adhesive, or epoxy.

93. A medical device comprising:

a manipulation assembly having a distal portion configured to be intravascularly positioned within a blood vessel lumen, the manipulation assembly comprising:

a tubular member configured to be coupled to a first electrical terminal, the tubular member having a proximal portion, a distal portion, and a lumen extending therein, wherein the distal portion of the tubular member comprises an aperture;

an elongate member configured to be coupled to a second electrical terminal, the elongate member extending through the lumen of the tubular member;

an insulating layer disposed between at least a portion of the tubular member and at least a portion of the elongate member; and an interventional element having a proximally located attachment portion, wherein when the interventional element is positioned in a first orientation, the attachment portion is slidably received within the aperture of the distal portion of the hypotube, and wherein when the attachment portion is positioned within the aperture and the interventional element is positioned in a second orientation, the attachment portion engages the tubular member.

94. The medical device of Clause 93, wherein the tubular member comprises a hypotube.

95. The medical device of Clause 93 or Clause 94, wherein the attachment portion of the interventional element comprises an arm and a protrusion thereon.

96. The medical device of Clause 95, wherein the arm is configured to be positioned within the aperture and the protrusion is configured to engage the tubular member.

97. The medical device of any one of Clauses 93 to 96, wherein when the attachment portion is positioned within the aperture and the interventional element is positioned in the second orientation, the attachment portion engages an internal surface of the tubular member.

98. The medical device of any one of Clauses 93 to 97, wherein the aperture has an oblong shape.

99. The medical device of any one of Clauses 93 to 98, wherein the second orientation is rotated approximately 90 degrees relative to the first orientation.

100. The medical device of any one of Clauses 93 to 99, wherein the interventional element forms an electrode.

101. The medical device of any one of Clauses 93 to 100, further comprising at least one electrode coupled to the interventional element.

102. The medical device of Clause 100 or Clause 101, wherein the electrode has a surface formed of gold.

103. The medical device of Clause 102, wherein the surface is an outer surface of the electrode.

104. The medical device of any one of Clauses 93 to 103, wherein the elongate member forms an electrode.

105. The medical device of any one of Clauses 93 to 104, further comprising at least one electrode coupled to the elongate member.

106. The medical device of Clause 104 or Clause 105, wherein the electrode has a surface formed of gold.

107. The medical device of Clause 106, wherein the surface is an outer surface of the electrode.

108. The medical device of any one of Clauses 93 to 107, further comprising a first electrode formed by or coupled to the interventional element and a second electrode formed by or coupled to the elongate member, wherein the first and second electrodes are configured to be of opposite polarities.

109. The medical device of any one of Clauses 93 to 108, wherein the elongate member provides a first current path through the aperture of the joining element which is insulated from a second current path conducted by the joining element to the interventional element.

110. The medical device of any one of Clauses 93 to 109, wherein a filler material is disposed within the aperture of the joining element.

111. The medical device of Clause 110, wherein the filler material comprises solder, adhesive, or epoxy.

112. A medical device comprising:

a manipulation assembly having a distal portion configured to be intravascularly positioned within a blood vessel lumen, the manipulation assembly comprising:

a tubular member configured to be coupled to a first electrical terminal, the tubular member having a proximal portion, a distal portion, and a lumen extending therein, wherein the distal portion of the tubular member comprises an aperture, and wherein the aperture comprises a first portion with a generally circular cross-sectional shape and a second portion with a generally rectangular cross-sectional shape;

a locking element having a lumen extending therethrough;

an elongate member configured to be coupled to a second electrical terminal, the elongate member extending through the lumen of the tubular member;

an insulating layer disposed between at least a portion of the tubular member and at least a portion of the elongate member; and an interventional element having a proximally located attachment portion, wherein the attachment portion is slidably received within the second portion of the aperture of the distal portion of the hypotube, and wherein when the attachment portion is positioned within the second portion of the aperture and the locking element is positioned within the first portion of the aperture, the attachment portion engages the tubular member and the locking element engages the tubular member and the attachment portion.

113. The medical device of Clause 112, wherein the tubular member comprises a hypotube.

114. The medical device of Clause 112 or Clause 113, wherein the attachment portion of the interventional element comprises an arm and a protrusion thereon.

115. The medical device of Clause 114, wherein the arm is configured to be positioned within the second portion of the aperture and the protrusion is configured to engage the tubular member.

116. The medical device of any one of Clauses 112 to 115, wherein when the attachment portion is positioned within the second portion of the aperture, the attachment portion engages an internal surface of the tubular member.

117. The medical device of any one of Clauses 112 to 116, wherein the first portion of the aperture has a generally circular cross-sectional shape and the second portion of the aperture has a generally rectangular cross-sectional shape.

118. The medical device of any one of Clauses 112 to 117, wherein the locking element is configured to prevent and/or limit rotation and radial displacement of the attachment portion within the aperture of the tubular member.

119. The medical device of any one of Clauses 112 to 118, wherein the interventional element forms an electrode.

120. The medical device of any one of Clauses 112 to 119, further comprising at least one electrode coupled to the interventional element.

121. The medical device of Clause 119 or Clause 120, wherein the electrode has a surface formed of gold.

122. The medical device of Clause 121, wherein the surface is an outer surface of the electrode.

123. The medical device of any one of Clauses 112 to 122, wherein the elongate member forms an electrode.

124. The medical device of any one of Clauses 112 to 123, further comprising at least one electrode coupled to the elongate member.

125. The medical device of Clause 123 or Clause 124, wherein the electrode has a surface formed of gold.

126. The medical device of Clause 125, wherein the surface is an outer surface of the electrode.

127. The medical device of any one of Clauses 112 to 126, further comprising a first electrode formed by or coupled to the interventional element and a second electrode formed by or coupled to the elongate member, wherein the first and second electrodes are configured to be of opposite polarities.

128. The medical device of any one of Clauses 112 to 127, wherein the elongate member provides a first current path through the aperture of the joining element which is insulated from a second current path conducted by the joining element to the interventional element.

129. The medical device of any one of Clauses 112 to 128, wherein a filler material is disposed within the aperture of the joining element.

130. The medical device of Clause 129, wherein the filler material comprises solder, adhesive, or epoxy.

131. A method of assembling a medical device comprising:

inserting a proximally located attachment portion of an interventional element through an aperture of a joining element, the joining element being coupled to a distal portion of an elongate manipulation member; and inserting a control member through the aperture alongside the attachment portion.

132. The method of Clause 131, further comprising, after inserting the attachment portion of the interventional element through the aperture, rotating the attachment portion with respect to the aperture.

133. The method of Clause 131 or Clause 132, wherein the attachment portion comprises a retention region and an engagement feature disposed proximal of the retention region, and wherein inserting the attachment portion through the aperture comprises passing the engagement feature completely through the aperture.

134. The method of any one of Clauses 131 to 133, wherein, after inserting the attachment portion through the aperture, the retention region is disposed within the aperture.

135. The method of any one of Clauses 131 to 134, further comprising affixing the control member with respect to the joining element via an adhesive.

136. The method of any one of Clauses 131 to 135, further comprising coupling the elongate manipulation member to a first electrical terminal of an extracorporeal power supply and coupling the control member to a second electrical terminal of the extracorporeal power supply.

137. A method of assembling a medical device comprising:

inserting a proximally located attachment portion of an interventional element into a first portion of an aperture of a joining element;

inserting a locking element into a second portion of the aperture of the joining element;

inserting a control member through a lumen of the locking element; and securing the joining element to a distal portion of an elongate manipulation member.

138. The method of Clause 137, wherein inserting the proximally located attachment portion of the interventional element into the first portion of the aperture of the joining element comprises inserting the attachment portion into the second portion of the aperture and radially displacing the attachment portion from the second portion of the aperture to the first portion of the aperture.

139. The method of Clause 137 or Clause 138, wherein inserting the locking element into the second portion of the aperture of the joining element comprises slidably passing the locking element into the second portion of the aperture.

140. The method of any one of Clauses 137 to 139, wherein securing the joining element to the distal portion of the elongate manipulation member comprises welding the joining element to the distal portion.

141. The method of any one of Clauses 137 to 140, wherein the attachment portion comprises a retention region and an engagement feature disposed proximal of the retention region, and wherein inserting the attachment portion through the aperture comprises passing the engagement feature completely through the aperture.

142. The method of any one of Clauses 137 to 141, wherein after inserting the attachment portion through the aperture, the retention region is disposed within the aperture.

143. The method of any one of Clauses 137 to 142, further comprising coupling the elongate manipulation member to a first electrical terminal of an extracorporeal power supply and coupling the control member to a second electrical terminal of the extracorporeal power supply.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

DETAILED DESCRIPTION

The present technology provides devices, systems, and methods for removing clot material from a blood vessel lumen. Although many of the embodiments are described below with respect to devices, systems, and methods for treating a cerebral or intracranial embolism, other applications and other embodiments in addition to those described herein are within the scope of the technology. For example, the treatment systems and methods of the present technology may be used to remove emboli from body lumens other than blood vessels (e.g., the digestive tract, etc.) and/or may be used to remove emboli from blood vessels outside of the brain (e.g., pulmonary, abdominal, cervical, or thoracic blood vessels, or peripheral blood vessels including those within the legs or arms, etc.). In addition, the treatment systems and methods of the present technology may be used to remove luminal obstructions other than clot material (e.g., plaque, resected tissue, foreign material, etc.).

Figure 1A:
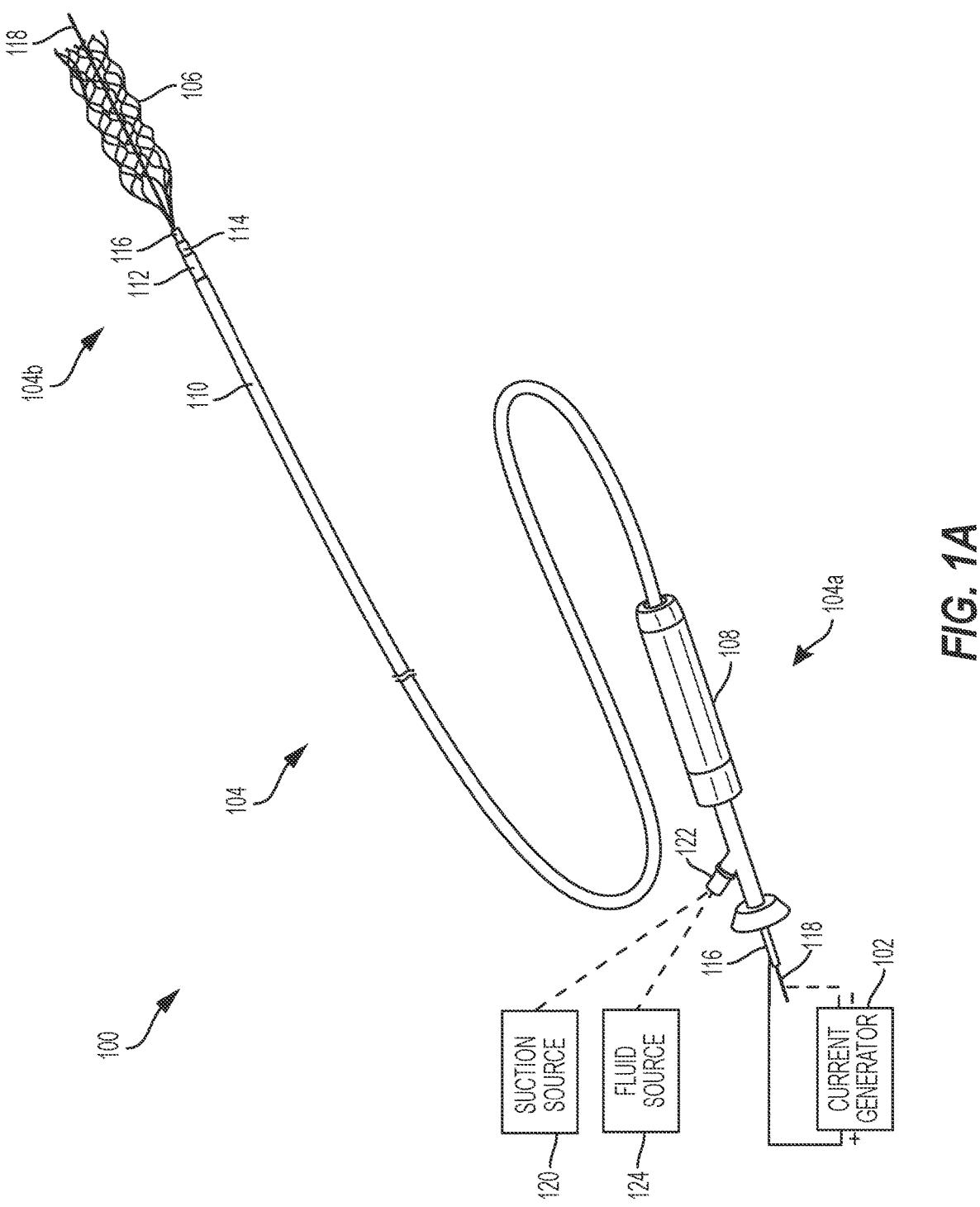
FIG. 1A shows a perspective view of an electrically enhanced treatment system for retrieving material from a body lumen, in accordance with one or more embodiments of the present technology.

FIG. 1A illustrates a view of an electrically enhanced treatment system 100 according to one or more embodiments of the present technology. As shown in FIG. 1A, the treatment system 100 can include a current generator 102 and a treatment device 104 having a proximal portion 104a configured to be coupled to the current generator 102 and a distal portion 104b configured to be intravascularly positioned within a blood vessel (such as an intracranial blood vessel). The distal portion 104b can be positioned within the blood vessel at a treatment site at or proximate a thrombus. The treatment device 104 includes an interventional element

106 at the distal portion 104*b*, a handle 108 at the proximal portion 104*a*, and a plurality of elongated shafts or members extending therebetween. For example, in some embodiments, such as that shown in FIG. 1A, the treatment device 104 includes a first catheter 110 (such as a guide catheter or balloon guide catheter), a second catheter 112 (such as a distal access catheter or aspiration catheter) configured to be slidably disposed within a lumen of the first catheter 110, a third catheter 114 (such as a microcatheter) configured to be slidably disposed within a lumen of the second catheter 112, a manipulation member 116 configured sized to be slidably disposed within a lumen of the third catheter 114, and a control member 118 configured to be disposed within a lumen of the manipulation member 116. In some embodiments, the treatment device 104 does not include the second catheter 112. The first catheter 110 can be coupled to the handle 108, which provides proximal access to the manipulation member 116 and control member 118. The current generator 102 may be coupled to a proximal portion of the manipulation member 116, and/or elsewhere on the proximal portion of the treatment device 104, to deliver electrical current to the interventional element 106 and thereby provide an electrically charged environment at the distal portion 104*b* of the treatment device 104, as described in more detail below. Further, the current generator 102 may be coupled to a proximal portion of the control member 118 to return electrical current from the electrically charged environment to the current generator 102.

In some embodiments, the treatment system 100 includes a suction source 120 (e.g., a syringe, a pump, etc.) configured to be fluidically coupled (e.g., via a connector 122) to a proximal portion of one or more of the first catheter 110, the second catheter 112, and/or the third catheter 114 to apply negative pressure therethrough. In some embodiments, the treatment system 100 includes a fluid source 124 (e.g., a fluid reservoir, a syringe, pump, etc.) configured to be fluidically coupled (e.g., via the connector 122) to a proximal portion of one or more of the first catheter 110, the second catheter 112, and/or the third catheter 114 to supply fluid (e.g., saline, contrast agents, a drug such as a thrombolytic agent, etc.) to the blood vessel.

According to some embodiments, the catheters 110, 112, and 114 can each be formed as a generally tubular member extending along and about a central axis. According to some embodiments, the third catheter 114 is generally constructed to track over a conventional guidewire in the cervical anatomy and into the cerebral vessels associated with the brain and may also be chosen according to several standard designs that are generally available. Accordingly, the third catheter 114 can have a length that is at least 125 cm long, and more particularly may be between about 125 cm and about 175 cm long. Other designs and dimensions are contemplated.

The second catheter 112 can be sized and configured to slidably receive the third catheter 114 therethrough. As noted above, the second catheter 112 can be coupled at a proximal portion to a suction source 120 (FIG. 1A) such as a pump or syringe in order to supply negative pressure to a blood vessel. The first catheter 110 can be sized and configured to slidably receive both the second catheter 112 and the third catheter 114 therethrough. In some embodiments, the first catheter 110 is a guide catheter or balloon guide catheter having an inflatable balloon or other expandable member surrounding the catheter shaft at or near its distal end. In operation the first catheter 110 can first be advanced through a vessel and then its balloon can be expanded to anchor the first catheter 110 in place and/or arrest blood flow from areas proximal of the balloon, e.g. to enhance the effectiveness of aspiration performed via the first catheter 110 and/or other catheter(s). Next, the second catheter 112 can be advanced through the first catheter 110 until its distal end extends distally beyond the distal end of the first catheter 110. The second catheter 112 can be positioned such that its distal end is adjacent a blood vessel (e.g., a site of a blood clot within the vessel). The third catheter 114 may then be advanced through the second catheter 112 until its distal end extends distally beyond the distal end of the second catheter 112. The interventional element 106 may then be advanced through the third catheter 114 via the manipulation member 116 for delivery to the blood vessel.

According to some embodiments, the bodies of the catheters 110, 112, and 114 can be made from various thermoplastics, e.g., polytetrafluoroethylene (PTFE or TEFLON®), fluorinated ethylene propylene (FEP), high-density polyethylene (HDPE), polyether ether ketone (PEEK), etc., which can optionally be lined on the inner surface of the catheters or an adjacent surface with a hydrophilic material such as polyvinylpyrrolidone (PVP) or some other plastic coating. Additionally, either surface can be coated with various combinations of different materials, depending upon the desired results.

According to some embodiments, the current generator 102 can include an electrical generator configured to output medically useful electric current. The current generator 102 can include a power source, a first terminal, a second terminal, and a controller. The controller includes a processor coupled to a memory that stores instructions (e.g., in the form of software, code or program instructions executable by the processor or controller) for causing the power source to deliver electric current according to certain parameters provided by the software, code, etc. The power source of the current generator 102 may include a direct current power supply, an alternating current power supply, and/or a power supply switchable between a direct current and an alternating current. The current generator 102 can include a suitable controller that can be used to control various parameters of the energy output by the power source or generator, such as intensity, amplitude, duration, frequency, duty cycle, and polarity. For example, the current generator 102 can provide a voltage of about 2 volts to about 28 volts and a current of about 0.5 mA to about 20 mA.

In some embodiments, instead of or in addition to a controller, the current generator 102 can include drive circuitry. In such embodiments, the current generator 102 can include hardwired circuit elements to provide the desired waveform delivery rather than a software-based generator. The drive circuitry can include, for example, analog circuit elements (e.g., resistors, diodes, switches, etc.) that are configured to cause the power source to deliver electric current via the first and second terminals according to the desired parameters. For example, the drive circuitry can be configured to cause the power source to deliver periodic waveforms via the first and second terminals.

The current generator 102 may be coupled to a proximal portion of the manipulation member 116, and/or a proximal portion of the third catheter 114, the second catheter 112, and/or first catheter 110 to provide an electric current to the interventional element 106. For example, as shown in FIG. 1A, the current generator 102 can be coupled to a proximal portion of the manipulation member 116 such that the manipulation member 116 functions as a delivery (e.g., positive) electrode or conductive path (i.e., transmitting current from the current generator to the blood vessel and/or treatment site). As shown in FIG. 1A, the current generator 102 can be coupled to a proximal portion of the control member 118 such that the control member 118 functions as a return (e.g., negative) electrode or conductive path (i.e., transmitting current from the blood vessel and/or treatment site to the current generator 102). In other embodiments, the return electrode can be separate from the control member. For example, the return electrode can be carried by one or more of the third catheter 114, the second catheter 112, and/or first catheter 110. In some embodiments, the return electrode can be provided via one or more external electrodes, such as a needle puncturing the patient, or a grounding pad applied to the patient's skin.

The system can include multiple (e.g., two or more), distinct conductive paths or channels for passing electrical current along the system. The interventional element 106 can serve as one electrode (e.g., the positive or delivery electrode) in electrical communication with a conductive path via the manipulation member 116. Another of the conductive paths of the system can be in electrical communication with another electrode (e.g., a negative or return electrode). For example, the control member 118 can serve as the negative or return electrode. The various embodiments of the manipulation member 116 can be configured to push and pull a device such as the interventional element 106 along the bodily lumen.

Figure 1B:
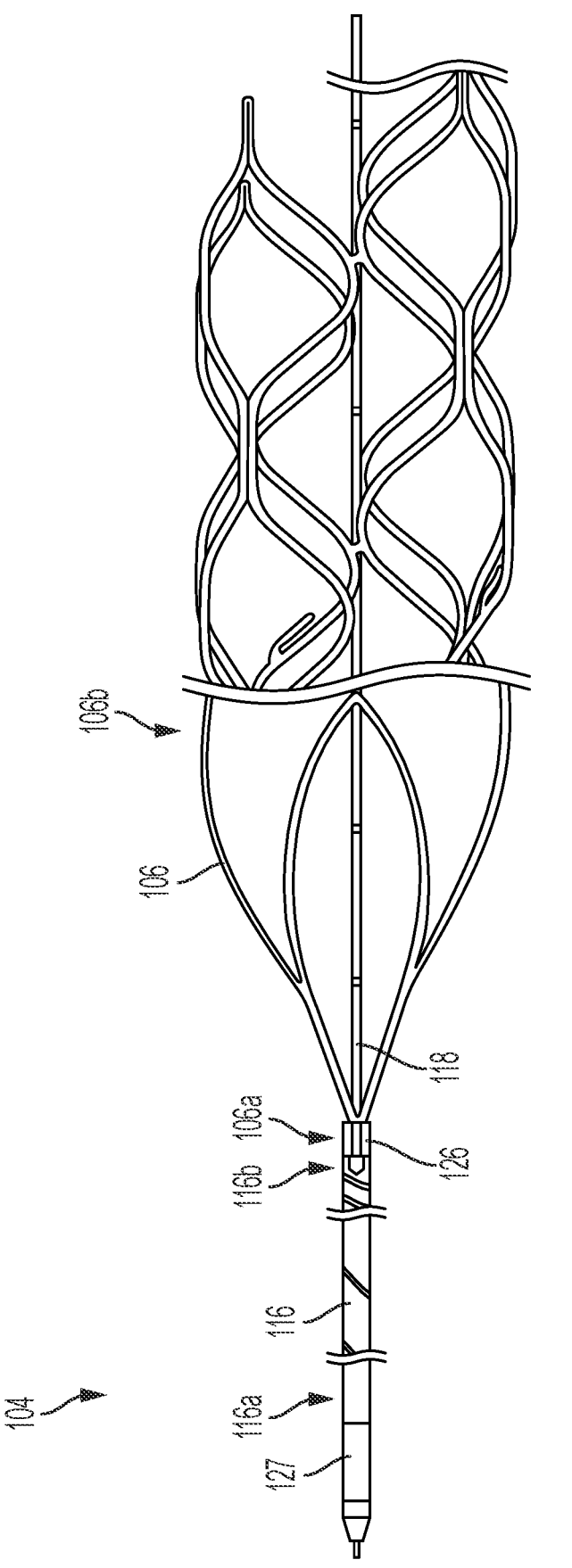
FIG. 1B is a side schematic view of the treatment device for retrieving material from a body lumen shown in FIG. 1A, in accordance with several embodiments of the present technology.

As noted above, the first terminal of the current generator 102 can be connected to a delivery electrode and the second terminal of the current generator 102 can be connected to a return electrode. For example, as shown in FIG. 1A, the manipulation member 116 can be connected to a positive terminal of the current generator 102 and the control member 118 can be connected to a negative terminal of the current generator 102. As shown in FIG. 1B, the manipulation member 116 and the interventional element 106 can be joined at a connection 126 to secure the interventional element 106 relative to the manipulation member 116 and to complete an electrical pathway between the elongate manipulation member 116 to the interventional element 106. The interventional element 106 can be metallic or electrically conductive so that when the interventional element 106 is placed in the presence of blood (or thrombus, and/or any other electrolytic medium which may be present, such as saline) and voltage is applied at the terminals of the current generator 102, current flows from the positive terminal of the current generator 102, distally along the manipulation member 116 to the interventional element 106 and through the surrounding media (e.g., blood, tissue, thrombus, etc.) before returning proximally along the control member 118 to the negative terminal of the current generator 102, thereby positively charging at least a portion of the interventional element 106 and promoting clot adhesion.

The current generator 102 can include a power source and either a processor coupled to a memory that stores instructions for causing the power source to deliver electric current according to certain parameters, or hardwired circuit elements configured to deliver electric current according to the desired parameters. The current generator 102 may be integrated into the manipulation member 116 and/or control member 118 or may be removably coupled to the manipulation member 116 and/or control member 118, for example via clips, wires, plugs or other suitable connectors.

In certain embodiments, the polarities of the current generator 102 can be switched, so that the negative terminal is electrically coupled to the manipulation member 116 and the positive terminal is electrically coupled to the control member 118. This can be advantageous when, for example, attempting to attract predominantly positively charged material to the interventional element 106, or when attempting to break up a clot rather than grasp it with an interventional element 106. In some embodiments alternating current (AC) signals may be used rather than DC. In certain instances, AC signals may advantageously help break apart a thrombus or other material.

In various embodiments, the interventional element 106 can take any number of forms, for example a removal device, a thrombectomy device, or other suitable medical device. For example, in some embodiments the interventional element 106 may be a stent and/or stent retriever, such as Medtronic's Solitaire™ Revascularization Device, Stryker Neurovascular's Trevo® ProVue™ Stentriever, or other suitable devices. In some embodiments, the interventional element 106 may be a coiled wire, a weave, and/or a braid formed of a plurality of braided filaments. Examples of suitable interventional elements 106 include any of those disclosed in U.S. Pat. No. 7,300,458, filed Nov. 5, 2007, U.S. Pat. No. 8,940,003, filed Nov. 22, 2010, U.S. Pat. No. 9,039,749, filed Oct. 1, 2010, and U.S. Pat. No. 8,066,757, filed Dec. 28, 2010, each of which is incorporated by reference herein in its entirety.

The interventional element 106 can have a low-profile, constrained or compressed configuration for intravascular delivery to the blood vessel within the third catheter 114, and an expanded configuration for securing and/or engaging clot material and/or for restoring blood flow in the blood vessel, for example at the treatment site. The interventional element 106 has a proximal portion including an attachment portion 106a that may be coupled to the manipulation member 116 and a distal portion comprising an open cell framework or body 106b. In some embodiments, the body 106b of the interventional element 106 can be generally tubular (e.g., cylindrical), and the proximal portion of the interventional element 106 can taper proximally to the attachment portion 106a.

The interventional element 106 can be a metallic and/or electrically conductive thrombectomy device. For example, the interventional element can include or be made of stainless steel, nitinol, cobalt-chromium, platinum, tantalum, alloys thereof, or any other suitable material. In some embodiments, the interventional element can have at least an outer surface of a highly conductive metal such as gold or copper; in some such embodiments, the entire interventional element is formed of gold or copper, and in other such embodiments the interventional element is formed from a first metal or alloy such as stainless steel, nitinol, etc. which is completely or partially plated or coated with a second metal or alloy such as gold or copper. In some embodiments, the interventional element 106 is a mesh structure (e.g., a braid, a stent, etc.) formed of a superelastic material (e.g., Nitinol) or other resilient or self-expanding material configured to self-expand when released from the third catheter 114. The mesh structure may include a plurality of struts and open spaces or cells formed by or located between the struts. In some embodiments, the struts and spaces may be situated along the longitudinal direction of the interventional element 106, the radial direction, or both.

The manipulation member 116 can be any suitable elongate member configured to advance the interventional element 106 to a treatment site within a blood vessel. For example, the manipulation member 116 can be or include a wire, tube (e.g., a hypotube), coil, or any combination thereof. According to some embodiments, the manipulation member 116 comprises an elongate tubular member defining a lumen therethrough. In some embodiments, the manipulation member 116 can comprise a distally located aperture configured to receive the attachment portion of the interventional element. In some embodiments, the manipulation member 116 comprises a distally located joining element comprising the aperture configured to receive the attachment portion. The manipulation member 116 can have a length sufficient to extend from a location outside the patient's body through the vasculature to a treatment site within the patient's body. The manipulation member 116 can be a monolithic structure or formed of multiple joined segments. In some embodiments, the manipulation member 116 can comprise a laser-cut hypotube having a spiral cut pattern (or other pattern of cut voids) formed in its sidewall along at least a portion of its length. The manipulation member 116 can be metallic and/or electrically conductive to deliver current from the current generator 102 to the interventional element 106. For example, the manipulation member 116 can comprise or consist of nickel titanium alloy, stainless steel, or other metals or alloys. In embodiments that comprise multiple joined segments, the segments may be of the same or different materials. For example, some or all of the manipulation member 116 can be formed of stainless steel, or other suitable materials known to those skilled in the art. Nickel titanium alloy may be preferable for kink resistance and reduction of imaging artifacts.

As described herein, the control member 118 can be configured to secure or retain a position of the interventional element 106 relative to the manipulation member. Additionally or alternatively, the control member 118 can be configured to function as a negative (e.g., return) electrode. The control member 118 can be any suitable elongate member configured to extend through a lumen of the manipulation member 116. For example, the control member 118 can be or include a wire, tube (e.g., a hypotube), coil, or any combination thereof. The control member 118 can have a length sufficient to extend from a location outside the patient's body through the vasculature to a treatment site within the patient's body. The control member 118 can be a monolithic structure or formed of multiple joined segments. The control member 118 can be metallic or electrically conductive to deliver current from the surrounding media (e.g., blood, tissue, thrombus, etc.) to the current generator 102. For example, the control member 118 can comprise or consist of nickel titanium alloy, stainless steel, or other metals or alloys. In embodiments that comprise multiple joined segments, the segments may be of the same or different materials. For example, some or all of the control member 118 can be formed of stainless steel, or other suitable materials known to those skilled in the art. Nickel titanium alloy may be preferable for kink resistance and reduction of imaging artifacts. The control member 118 can be electrically insulated along some or all of its length. In some embodiments, the control member 118 comprises an insulated wire or guide wire having one or more exposed, electrically conductive portions. For example, a distal end portion of the control member 118 can be exposed to conduct current from surrounding media (e.g., blood, tissue, thrombus, etc.) at a treatment site. In some such embodiments, the conductive element of the control member 118 can have at least an outer surface of a highly conductive metal such as gold or copper, so as to form gold or copper electrodes where insulation is removed or omitted. When implementing this, the entire conductive element of the control member can be formed of gold or copper, or it can be formed from a first metal or alloy such as stainless steel, nitinol, etc. which is completely or partially plated, coated or surrounded (e.g. in the form of a drawn-filled tube) with a second metal or alloy such as gold or copper. This can be done in combination with a gold or copper outer surface of the interventional element 106 such that all electrode surfaces are of a single metal or alloy such as gold, or copper, or other desired conductive metal or alloy.

In some embodiments, the treatment device 104 can comprise one or more electrically insulating materials. For example, an insulating material can be disposed on one or more portions of the control member 118 to electrically isolate the control member 118 from the manipulation member 116, the connection 126, and/or the interventional element 106. Additionally or alternatively, an insulating material can be disposed within a lumen of the manipulation member 116 to electrically isolate the manipulation member 116 from the control member 118 and/or the attachment portion of the interventional element 106. In some embodiments, an insulating material is disposed over an outer surface of the manipulation member 116 along at least a portion of a length of the manipulation member 116 to direct current through the manipulation member 116 and prevent and/or limit current loss from the manipulation member 116 to the surrounding environment. As shown in FIG. 1B, in some embodiments, an insulating material 127 can be disposed adjacent to a proximal end portion 116a and/or a distal end portion 116b of the manipulation member 116. The insulating material may be disposed along an entire length of the manipulation member 116 and/or the control member 118 or the insulating material may be disposed along select portions of the manipulation member 116 and/or the control member 118. The insulating material may comprise polyimide, parylene, PTFE, or another suitable electrically insulating material.

Figure 1C:
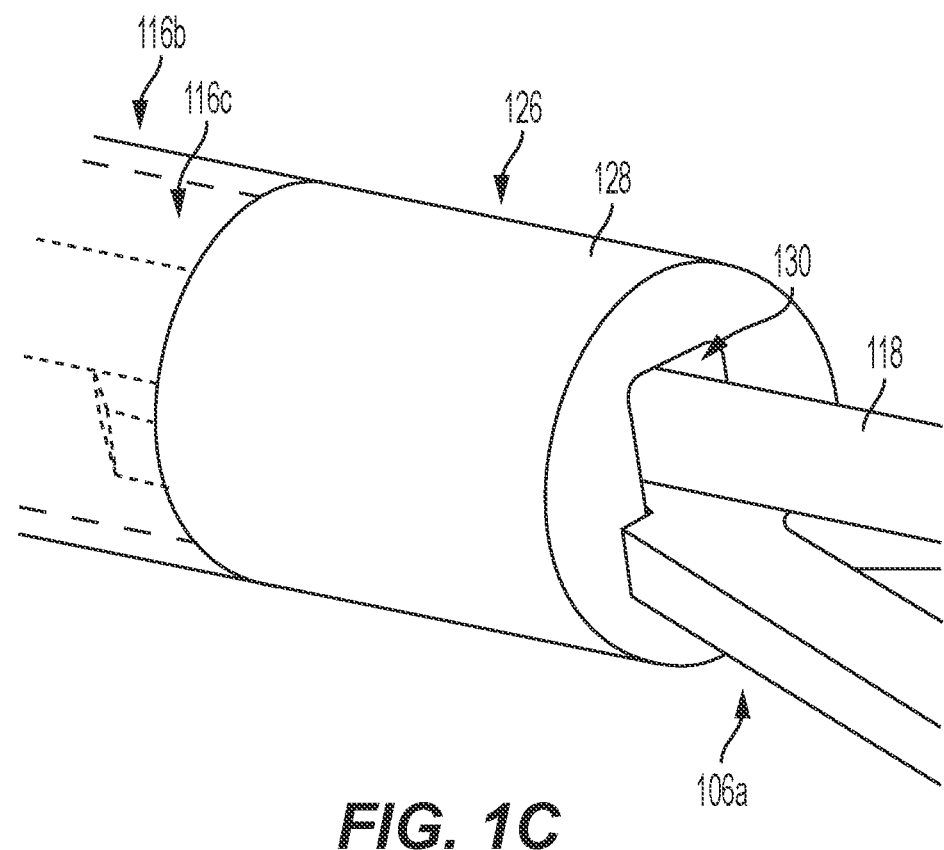
FIG. 1C is an isometric view of an interventional element and an elongate member positioned within a joining element in accordance with several embodiments of the present technology.

As shown in FIGS. 1B and 1C, the interventional element 106 and the manipulation member 116 can be coupled at a connection 126. According to some embodiments, the interventional element 106 and the manipulation member 116 can be substantially permanently attached together at the connection 126. That is, the interventional element 106 and the manipulation member 116 can be attached together in a manner that, under the expected use conditions of the device, the interventional element 106 and the manipulation member 116 would not become unintentionally separated from one another. In some embodiments, the treatment device 104 can comprise a portion, located proximally or distally of the connection 126, that is configured for selective detachment of the interventional element 106 from the manipulation member 116. For example, such a portion can comprise an electrolytically severable segment of the manipulation member 116. In some embodiments, the device can be devoid of any feature that would permit selective detachment of the interventional element 106 from the manipulation member 116. As described in more detail elsewhere herein, the connection 126 can provide a mechanical interlock between the interventional element 106 and the manipulation member 116. Moreover, the connection 126 can be configured to complete an electrically conductive path between the interventional element 106 and the elongate manipulation member 116.

FIG. 1C illustrates an enlarged perspective view of the connection 126, according to some embodiments, between the manipulation member 116 and the interventional element 106. In some embodiments, for example as shown in FIG. 1C, the manipulation member 116 comprises a distally located joining element 128 including an aperture 130 configured to receive a proximally located attachment portion 106a of the interventional element and/or at least a portion of the control member 118. As shown in FIG. 1C, the attachment portion 106a of the interventional element 106 is configured to mechanically interlock with a joining element 128 to secure the interventional element 106 to the manipulation member 116. According to some embodiments, the control member 118 can be disposed within the aperture at a radially adjacent position relative to the attachment portion 106a to facilitate such securement. Further, the control member 118 may be affixed to the joining element 128 via an adhesive.

In some embodiments, the connection 126 can comprise a bonding agent in addition or alternative to the joining element 128 and/or control member 118. The bonding agent can comprise adhesive, solder, welding flux, brazing filler, etc. In some embodiments, the bonding agent can bond to the connection 126 without applying heat. For example, the bonding agent can comprise a UV-curable adhesive. In embodiments that comprise a polymer coating of the wire or polymer tubing, use of a bonding agent that avoids application of heat that would damage the polymer may be preferred.

Figure 2A:
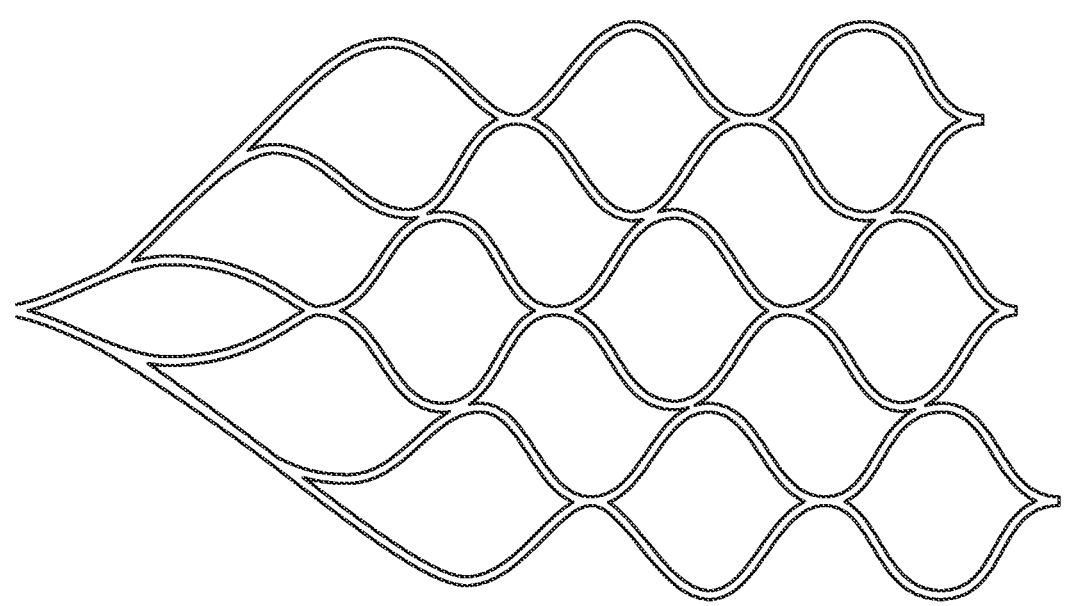
FIG. 2A is a plan view of an interventional element in an unfurled configuration in accordance with several embodiments of the present technology.
Figure 2B:
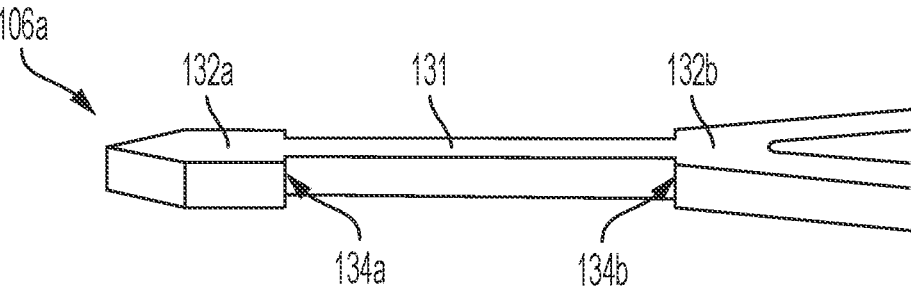
FIGS. 2B, 2C, and 2D are isometric, plan, and side views, respectively, of the interventional element shown in FIG. 2A.
Figure 2C:
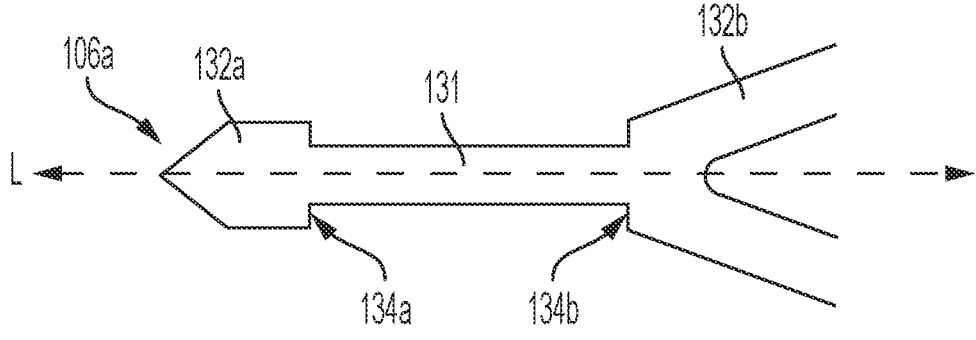
Figure 2D:
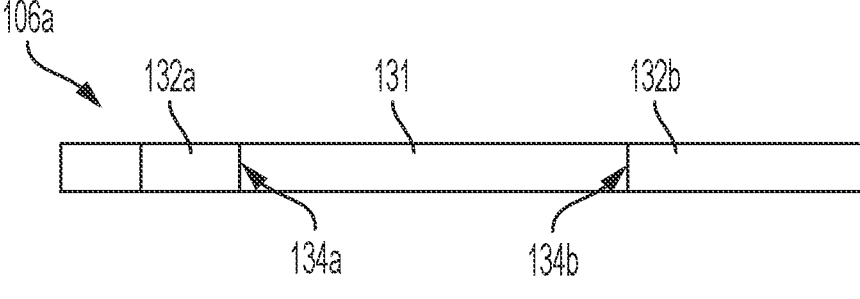

FIG. 2A is a plan view of the interventional element 106, depicted in an unfurled or flattened configuration for ease of understanding, and FIGS. 2B-2D are enlarged detail views of the attachment portion 106a of the interventional element 106. As previously described, the interventional element 106 has a proximal portion that may be coupled to the manipulation member 116 and a distal portion. The interventional element 106 has a proximal portion including an attachment portion 106a that may be coupled to the manipulation member 116 and a distal portion comprising an open cell framework or body 106b. The attachment portion 106a of the interventional element 106 can have a substantially constant thickness, such as would result from the interventional element 106 being cut from a tube or sheet of material, for example. In other embodiments, the thickness of the attachment portion 106a can vary across its length, width, or both.

The attachment portion 106a can comprise a retention region 131 and one or more engagement features 132 (e.g., proximal engagement feature 132a, distal engagement feature 132b). The retention region 131 can comprise a projection or arm extending proximally of the body 106b of the interventional element 106. Each of the one or more engagement features 132 can comprise a protrusion, flange, bump, ridge, shoulder, barb, or other suitable structural feature. In some embodiments, one or more engagement features 132 extend radially or laterally outwardly away from the retention region 131 and/or away from a central longitudinal axis L of the device. The attachment portion 106a can comprise any suitable number of engagement features 132 at any suitable location with respect to the retention region 131. For example, although FIGS. 2A-2D depict the proximal engagement feature 132a disposed at a proximal terminus of the retention region 131, each of the one or more engagement features 132 can be positioned at any suitable location with respect to the retention region 131. In some embodiments, the attachment portion 106a comprises more than one retention region 131.

The retention region 131 can optionally be configured to be radially or laterally biased such that the retention region 131 maintains a residual spring tension or outward pre-load or bias when engaged with the joining element 128. This is because the joining element 128 can prevent and/or limit the retention region 131 from moving laterally outward to the rest or unbiased position that the retention region 131 would otherwise occupy. The resulting residual tension can increase the stability of the connection 126.

The proximal engagement feature 132a and/or the distal engagement feature 132b can have a greatest cross-sectional dimension that is larger than a greatest cross-sectional dimension of the retention region 131. In some embodiments, the greatest cross-sectional dimension is a maximum lateral dimension that is measured in a direction perpendicular to a longitudinal axis L, extending in a proximal-distal direction, of the device. Accordingly, as shown in FIGS. 2A-2D, the proximal engagement feature 132a can comprise a distal-facing surface 134a and the distal engagement feature 132b can comprise a proximal-facing surface 134b. The distal-facing surface 134a and/or the proximal-facing surface 134b distal-facing surface can form a shoulder, planar surface, flange, or other suitable engagement surface that is configured to abut or otherwise engage with a corresponding engagement surface of the joining element 128. For example, the distal-facing surface 134a can be positioned to abut a proximal-facing surface (e.g., a proximal end surface) of the joining element 128 and the proximal-facing surface 134b can be positioned to abut a distal-facing surface (e.g., a distal end surface) of the joining element 128. In some embodiments, the distal-facing surface 134a and/or the proximal-facing surface 134b extends outwardly (e.g., radially, laterally, and/or circumferentially outwardly) from the retention region 131. In some embodiments, the distal-facing surface 134a and/or the proximal-facing surface 134b forms an oblique angle with the longitudinal axis L of the device, for example being substantially orthogonal to the longitudinal axis L of the device.

Figure 3A:
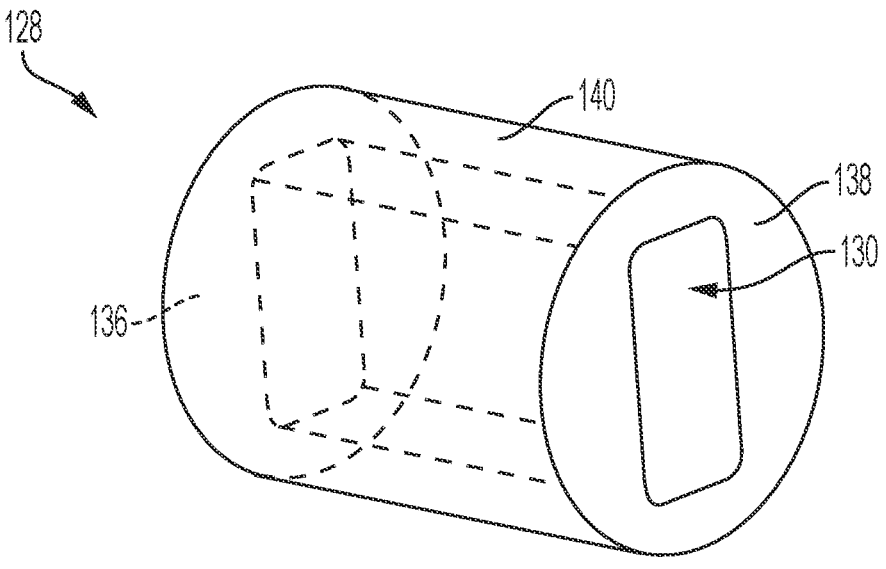
FIGS. 3A and 3B are isometric and end views, respectively, of a joining element in accordance with several embodiments of the present technology.
Figure 3B:
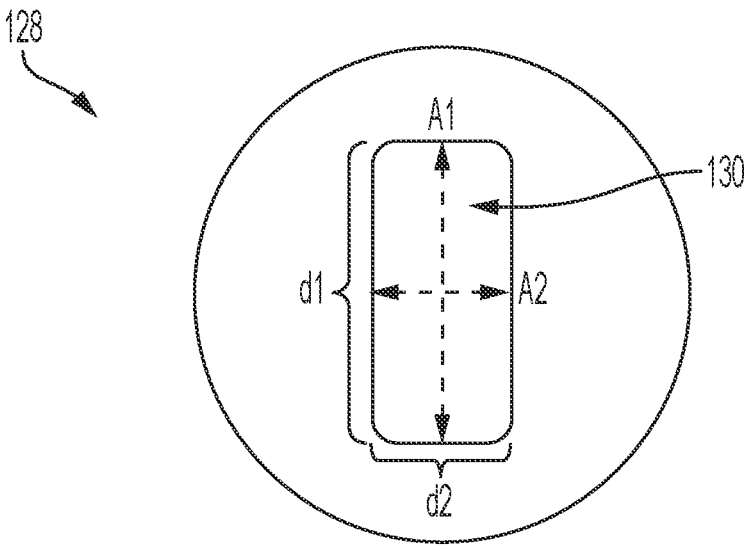

FIGS. 3A and 3B illustrate an embodiment of the joining element 128 in accordance with the present technology. As shown in FIGS. 3A and 3B, the joining element 128 can comprise a first end surface 136, a second end surface 138 opposite the first end surface along a length of the joining element, a sidewall 140 therebetween, and an aperture 130 extending from the first end surface 136 to the second end surface 138. The sidewall 140 can be generally annular and/or the first and second end surfaces 136, 138 can have a generally circular cross-sectional shape such that the joining element 128 has an overall generally cylindrical shape. The joining element 128 can comprise a circumferential element such as a band, collar, coil, etc. The joining element 128 can be configured to surround all or a portion of the length of the retention region 131. In some embodiments, the joining element 128 is circumferentially discontinuous. As shown in FIGS. 3A and 3B, the aperture 130 can have a first cross-sectional dimension d1 along a first direction A1 that is greater than a second cross-sectional dimension d2 along a second direction A2 orthogonal to the first direction A1. For example, the aperture 130 can have a generally oblong cross-sectional shape (e.g., ovular, rectangular, etc.). In some embodiments, the first and second directions A1, A2 are radial or lateral directions.

The joining element 128 can be positioned at the distal end portion 116b of the manipulation member 116. As described herein, the joining element 128 can be configured to be coupled to the manipulation member 116. In some embodiments, the joining element 128 is configured such that the first end surface 136 is proximal-facing and the second end surface 138 is distal-facing. The first end surface 136 can be configured to be coupled to the distal end portion 116b of the manipulation member 116. The joining element 128 can be coupled to the manipulation member via welding, adhesive, crimping, insertion, interference fit, or another suitable process or technique. In some embodiments, the joining element 128 is electrically coupled to the manipulation member 116. Accordingly, the joining element 128 can comprise an electrically conductive material. In some embodiments, the joining element 128 is configured to serve as a radiopaque marker and can be formed of a radiopaque material such as, for example, platinum or platinum alloys, including platinum-iridium. Additionally or alternatively, the joining element 128 can comprise a material such steel or steel alloys, including stainless steel, or aluminum or aluminum alloys. In some embodiments, the joining element 128 and manipulation member 116 comprise a monolithic structure.

The joining element 128 can have a greatest radial dimension (e.g., an outer diameter) that is substantially similar to a greatest radial dimension (e.g., an outer diameter) of the manipulation member 116. In some embodiments, the first cross-sectional dimension d1 and/or the second cross-sectional dimension d2 of the aperture 130 of the joining element 128 are less than a cross-sectional dimension of the lumen 116c of the manipulation member 116 such that, when the joining element 128 is coupled to the manipulation member 116, the first end surface 136 of the joining element 128 obstructs a portion of the lumen 116c of the manipulation member 116 and provides an engagement surface for the attachment portion 106a of the interventional element 106 to engage with.

Figure 4A:
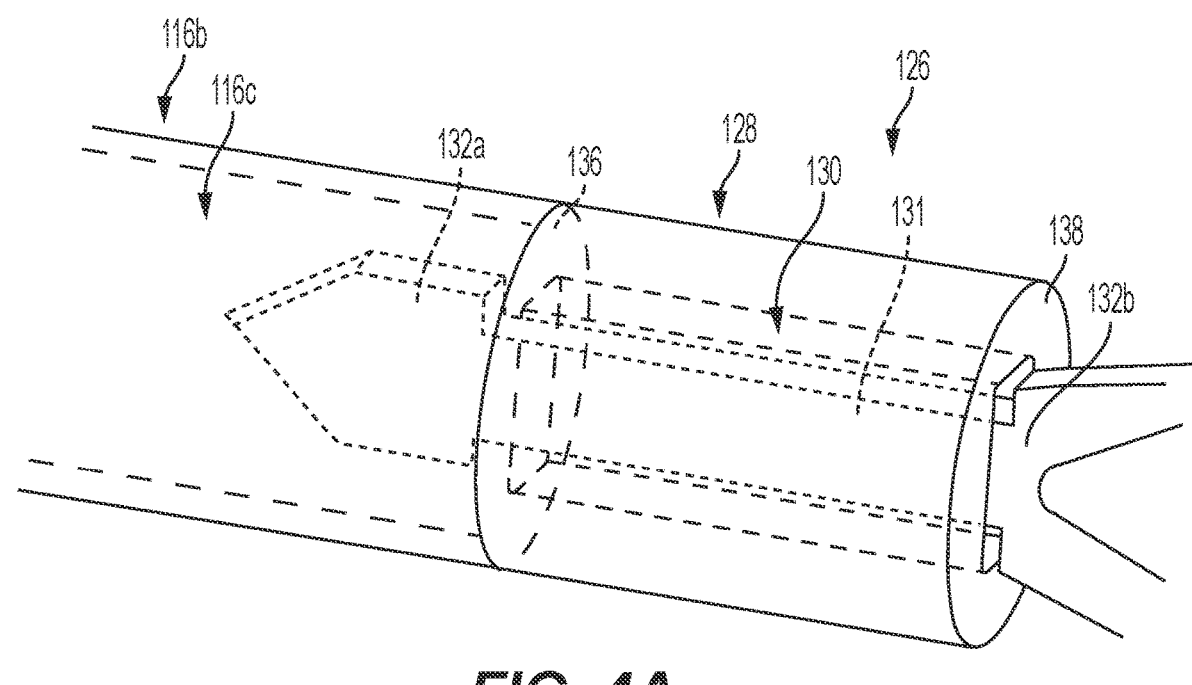
FIGS. 4A and 4B are isometric and side views, respectively, of a connection between a manipulation member and an interventional element via a joining element in accordance with several embodiments of the present technology.
Figure 4B:
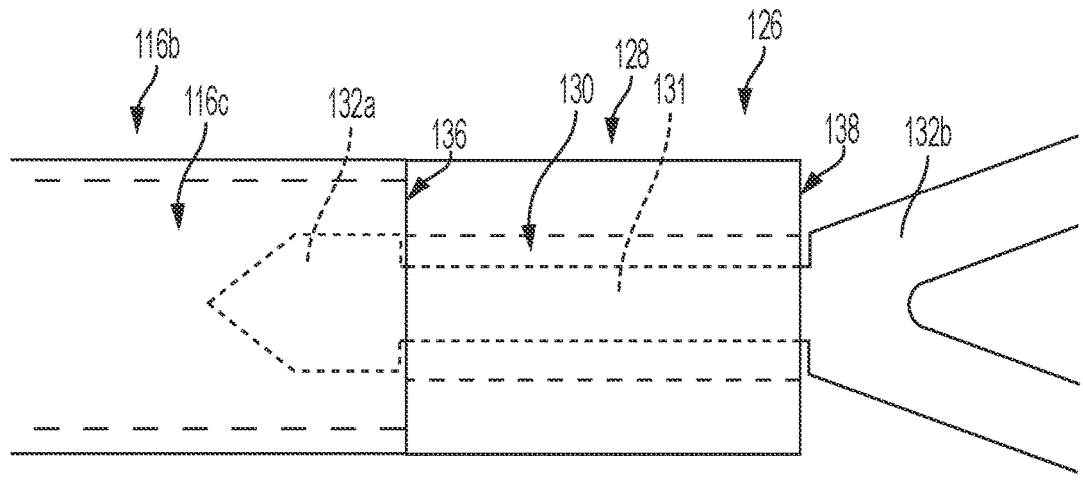

The retention region 131 of the attachment portion 106a of the interventional element 160 can have a greatest cross-sectional dimension that is less than a smallest cross-sectional dimension of the aperture (e.g., the second cross-sectional dimension d2). The proximal engagement feature 132a and/or the distal engagement feature 132b can have a greatest cross-sectional dimension that is less than the first cross-sectional dimension d1 of the aperture 130 and greater than the second cross-sectional dimension d2 of the aperture 130. Accordingly, as shown in FIGS. 4A and 4B, the attachment portion 106a can be configured to be inserted into the aperture of the joining element 128 when the attachment portion 106a is positioned in a first orientation in which the greatest cross-sectional dimension of the proximal engagement feature 132a and/or the distal engagement feature 132b is aligned with the first cross-sectional dimension d1 of the aperture 130. In such embodiments, the attachment portion 106a may be slidably passed into the aperture 130 such that the retention region 131 is positioned at least partially within the aperture 130 and the proximal engagement feature 132a is positioned proximal of the joining element 128 within the lumen 116c of the manipulation member 116 (again, as depicted in FIGS. 4A-4B).

Figure 5A:
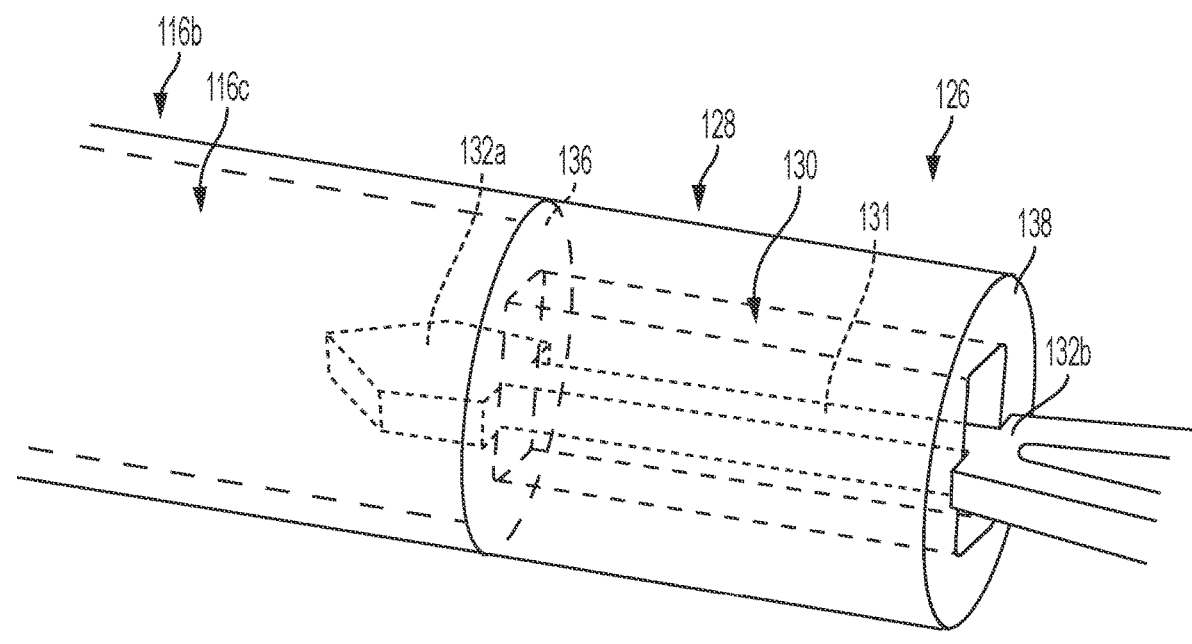
FIGS. 5A and 5B are isometric and side views, respectively, of a connection between a manipulation member and an interventional element in accordance with several embodiments of the present technology.
Figure 5B:
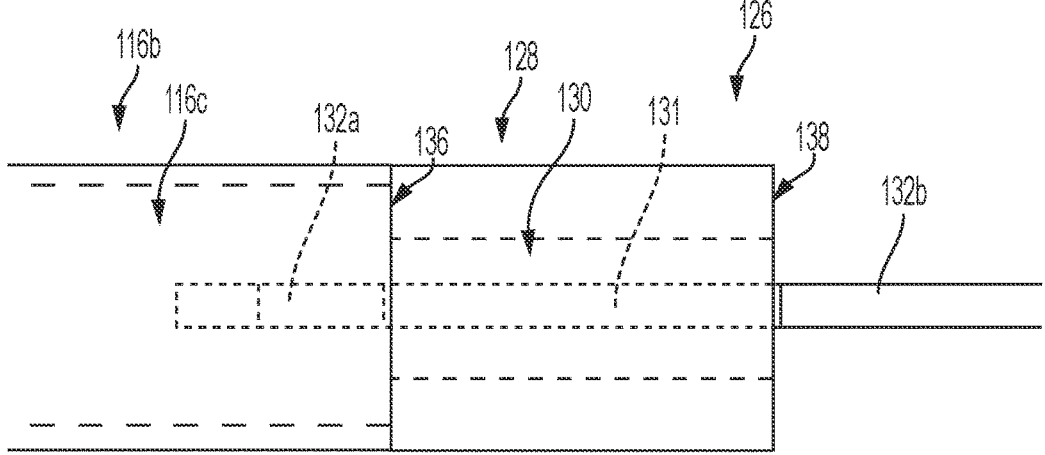

To mechanically interlock the attachment portion 106a of the interventional element 106 with the joining element 128, the attachment portion 106a can be moved from the first orientation to a second orientation (see FIGS. 5A and 5B). For example, the attachment portion 106a can be rotated in a circumferential direction approximately about the longitudinal axis of the manipulation member 116, such that the greatest cross-sectional dimension of the proximal engagement feature 132a and/or the distal engagement feature 132b is aligned with the second (smaller) cross-sectional dimension d2 of the aperture 130. In embodiments in which the greatest cross-sectional dimension of the proximal engagement feature 132a is greater than the second cross-sectional dimension d2 of the aperture 130, for example as shown in FIGS. 5A and 5B, the proximal engagement feature 132a can be configured to engage the first end surface 136 of the joining element 128. Similarly, in embodiments in which the greatest cross-sectional dimension of the distal engagement feature 132b is greater than the second cross-sectional dimension d2 of the aperture 130, for example as shown in FIGS. 5A and 5B, the distal engagement feature 132b can be configured to engage the second end surface 138 of the joining element 128. Additionally or alternatively, the proximal engagement feature 132a and/or the distal engagement feature 132b may be configured to engage the aperture 130 of the joining element 128. The proximal engagement feature 132a may be configured to avoid contact with a wall of the lumen 116c of the manipulation member 116 or to contact a wall of the lumen 116c of the manipulation member 116. The engagement features 132 can be configured to prevent and/or limit motion (e.g., longitudinal movement) of the interventional element 106 relative to the joining element 128 and thereby the manipulation member 116. For example, as shown in FIGS. 5A and 5B, the proximal engagement feature 132a can be configured to abut the first end surface 136 (i.e., the proximal-facing surface) of the joining element 128 when the retention region 131 is positioned within the aperture 130 to thereby prevent and/or limit distal translation of the interventional element 106 with respect to the joining element 128. Similarly, the distal engagement feature 132b can be configured to abut the second end surface 138 (i.e., the distal-facing surface) of the joining element 128 when the retention region 131 is positioned within the aperture 130 to thereby prevent and/or limit proximal translation of the interventional element 106 with respect to the joining element 128. Additionally or alternatively, each of the engagement features 132 can be configured to prevent and/or limit distal translation, proximal translation, and/or rotation of the interventional element 106 with respect to the joining element 128. In addition to securing the interventional element 106 to the manipulation member 116, the mechanical interlock and contact between the attachment portion 106a and the joining element 128 is configured to electrically couple the attachment portion 106a to the joining element 128 such that current supplied to the manipulation member 116 may pass to the interventional element 106 via the joining element 128.

In some embodiments, a control member (e.g., control member 118 as shown in FIG. 2A) can be inserted through the aperture 130 after the attachment portion 106a of the interventional element 106 has been moved to the second orientation. For example, the attachment portion 106a can be rotated with respect to the joining element 128 (as shown in FIG. 5B), and then an elongate control member can be slidably inserted through the aperture 130 at a position radially adjacent the attachment portion 106a. By occupying this space within the aperture, the control member can inhibit the attachment portion 106a from reverting to the first orientation (e.g., precluding the attachment portion 106a from rotating with respect to the joining element 128). As noted previously, in some embodiments the control member can also serve as a negative (e.g., return) electrode, for example taking the form of an elongated wire that is insulated along at least a portion of its length, with one or more exposed portions of the wire that are configured to contact electrolytic media, such as blood, while positioned at the treatment site. In some embodiments, a bonding agent (e.g., weld, adhesive, solder, etc.) can be applied to some or all of the control member, joining element 128, and/or attachment portion 106a after they have been moved into position such that the joining element 128, attachment portion 106a, and control member are substantially permanently connected. In some embodiments, the control member 118 may be omitted from the aperture 130, and a filler material such as solder, adhesive, epoxy, etc., or some other element, may be placed in the portion(s) of the aperture 130 not occupied by the retention region 131 in order to prevent the retention region 131 from exiting the aperture 130.

Figure 6:
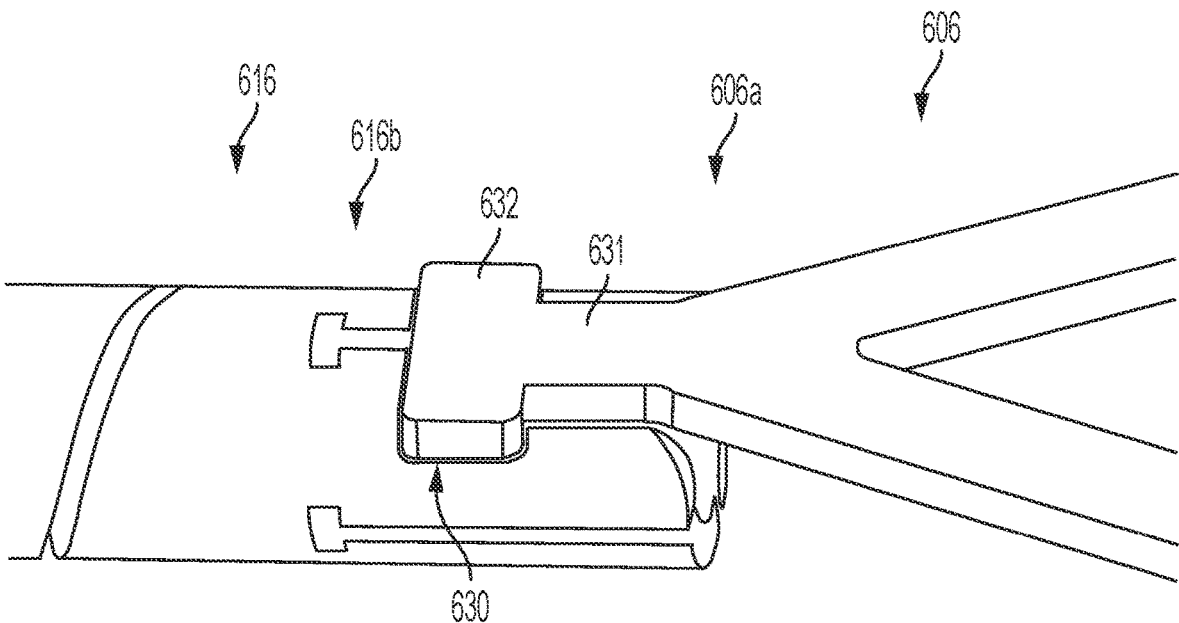
FIG. 6 is an isometric view of a connection between a manipulation member and an interventional element in accordance with several embodiments of the present technology.

According to some embodiments, for example as shown in FIG. 6, a manipulation member 116 is comprises an aperture 630 configured to receive an attachment portion 606*a* of an interventional element 606. The aperture 630 may be positioned at or near a distal end portion 616*b* of the manipulation member 616. In such embodiments, the manipulation member 116 may not comprise a distally located joining element. As described herein, the attachment portion 606*a* can comprise a retention region 631 and an engagement feature 632. In some embodiments, the attachment portion 606*a* is configured to be slidably inserted into the aperture 630 along a first direction. Once inserted, the engagement feature 632 can be configured to engage with the manipulation member 116 such the attachment portion 606*a* and the manipulation member 616 are mechanically interlocked. The mechanical interlock between attachment portion 606*a* and the manipulation member 616 can be configured to limit motion of the interventional element 606 with respect to the manipulation member 616 along a second direction. For example, the attachment portion 606*a* can be configured to be inserted into the aperture 630 along a radial dimension of the manipulation member 616 such that motion of the interventional element 606 is limited with respect to the manipulation member 616 along a longitudinal axis of the manipulation member 616 (e.g., in a proximal direction or in a distal direction). In some embodiments, the second direction can be the same as the first direction. Additionally or alternatively, the attachment portion 606*a* can be configured to be rotated in a radial direction once inserted into the aperture 630 to engage the manipulation member 616, as described herein. As with the embodiments described previously with respect to FIGS. 4A-5B, an elongated control member (e.g., control member 118) can be slidably inserted through the lumen of the manipulation member 616 and configured to retain the attachment portion 606*a* of the interventional element 606 in place with respect to the manipulation member 616.

Figure 7A:
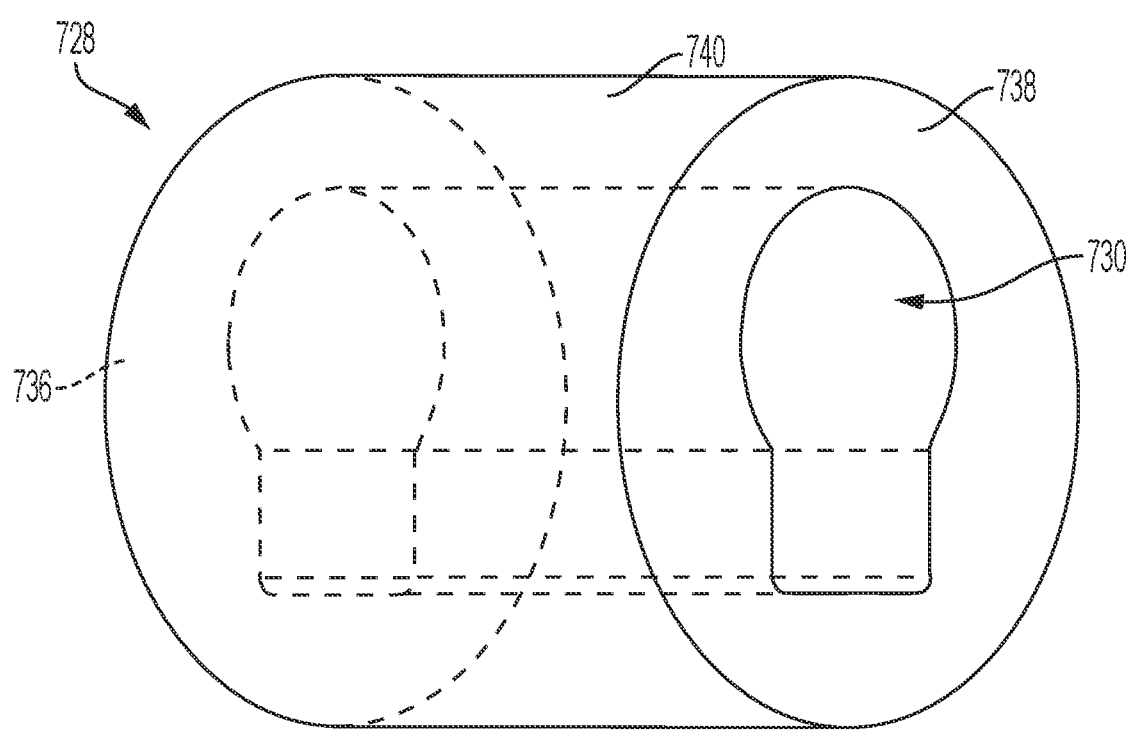
FIGS. 7A and 7B are isometric and end views, respectively, of a joining element in accordance with several embodiments of the present technology.
Figure 7B:
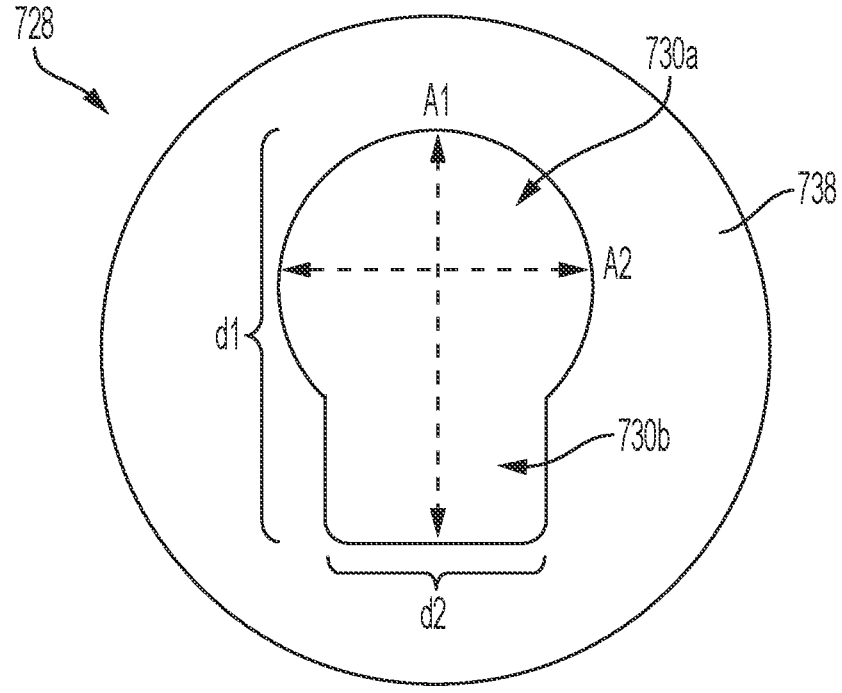

FIGS. 7A and 7B illustrate a joining element 728 configured in accordance with several embodiments of the present technology. In some embodiments, the joining element 728 can be similar to any of the embodiments of the joining element 128 disclosed herein, except as further described. As with the embodiments described previously with respect to FIGS. 1A-5B, the joining element 728 can be configured to be positioned at and/or coupled to a distal end portion of a manipulation member (e.g., distal end portion 116*b* of manipulation member 116) and can be configured to retain an attachment portion of an interventional element (e.g., attachment portion 106*a* of interventional element 106) in place with respect to the manipulation member. As shown in FIGS. 7A and 7B, the joining element 728 can comprise a first end surface 736, a second end surface 738 opposite the first end surface along a length of the joining element, a sidewall 740 therebetween, and an aperture 730 extending from the first end surface 736 to the second end surface 738. The sidewall 740 can be generally annular and/or the first and second end surfaces 736, 738 can have a generally circular cross-sectional shape such that the joining element 728 has an overall generally cylindrical shape. The joining element 728 can comprise a circumferential element such as a band, collar, coil, etc. The joining element 728 can be configured to surround all or a portion of the length of a retention region of an attachment portion of an interventional element (e.g., retention region 131). In some embodiments, the joining element 728 is circumferentially discontinuous. The joining element 728 can comprise a radiopaque material such as, for example, platinum or platinum alloys, including platinum-iridium. Additionally or alternatively, the joining element 728 can comprise a material such steel or steel alloys, including stainless steel, or aluminum or aluminum alloys, or titanium, or nickel-titanium alloy such as nitinol.

The aperture 730 can comprise a first portion 730*a* with a first cross-sectional shape and a second portion 730*b* with a second cross-sectional shape. For example, as shown in FIGS. 7A and 7B the first portion 730*a* can have a generally circular first cross-sectional shape and the second portion 730*b* can have a generally rectangular second cross-sectional shape. The first and second cross-sectional shapes can be different from one another in shape (e.g., as shown in FIGS. 7A and 7B, etc.) or similar to one another in shape (e.g., both the first and second cross-sectional shapes can be generally rectangular, etc.).

The aperture 730 can have a first cross-sectional dimension d1 along a first direction A1 and a second cross-sectional dimension d2 along a second direction A2 orthogonal to the first direction A1. In some embodiments, the first and second directions A1, A2 are radial or lateral directions. In some embodiments, the second cross-sectional dimension d2 varies along the second direction A2. For example, as shown in FIGS. 7A and 7B, the second cross-sectional dimension d2 can be greater at the first portion 730*a* of the aperture 730 than the second cross-sectional dimension d2 at the second portion 730*b* of the aperture 730. In some embodiments, the first cross-sectional dimension d1 is greater than the second cross-sectional dimension d2 at one or more locations along the first direction A1.

Figure 8A:
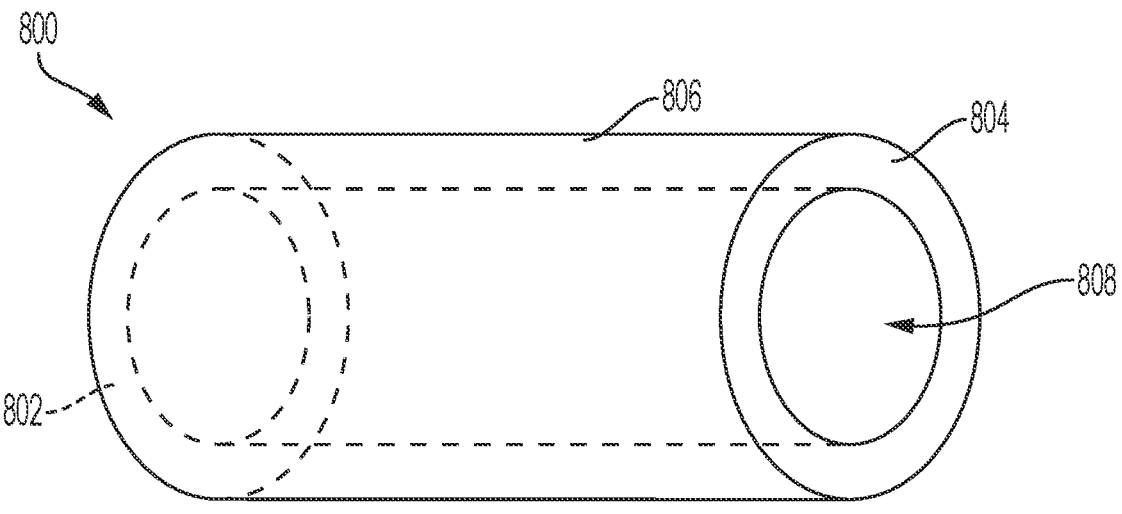
FIGS. 8A and 8B are isometric and end views, respectively, of a locking element in accordance with several embodiments of the present technology.
Figure 8B:
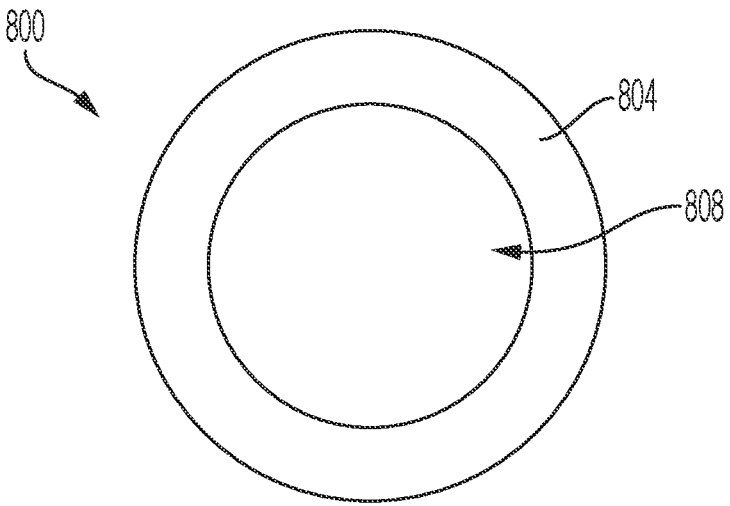

In some embodiments, the aperture 730 of the joining element 728 can be configured to receive a locking element therein to facilitate mechanical interlocking of the joining element 728 with an attachment portion of an interventional element. FIGS. 8A and 8B illustrate a locking element 800 configured in accordance with several embodiments of the present technology. The locking element 800 can comprise a first end surface 802, a second end surface 804 opposite the first end surface 802 along a length of the locking element 800, a sidewall 806 therebetween, and an aperture 808 extending from the first end surface 802 to the second end surface 804. As described in greater detail herein, in some embodiments the sidewall 806 is generally annular.

The locking element 800 can comprise a radiopaque material such as, for example, platinum or platinum alloys, including platinum-iridium. Additionally or alternatively, the locking element 800 can comprise a material such as steel or steel alloys, including stainless steel, or aluminum or aluminum alloys, or titanium, or nickel-titanium alloy such as nitinol. In some embodiments, the locking element 800 comprises a polymeric material or a ceramic material. The locking element 800 can comprise a mesh, a wire, a coil, or another suitable structure configured to inhibit motion of the attachment portion with respect to the joining element.

Figure 9A:
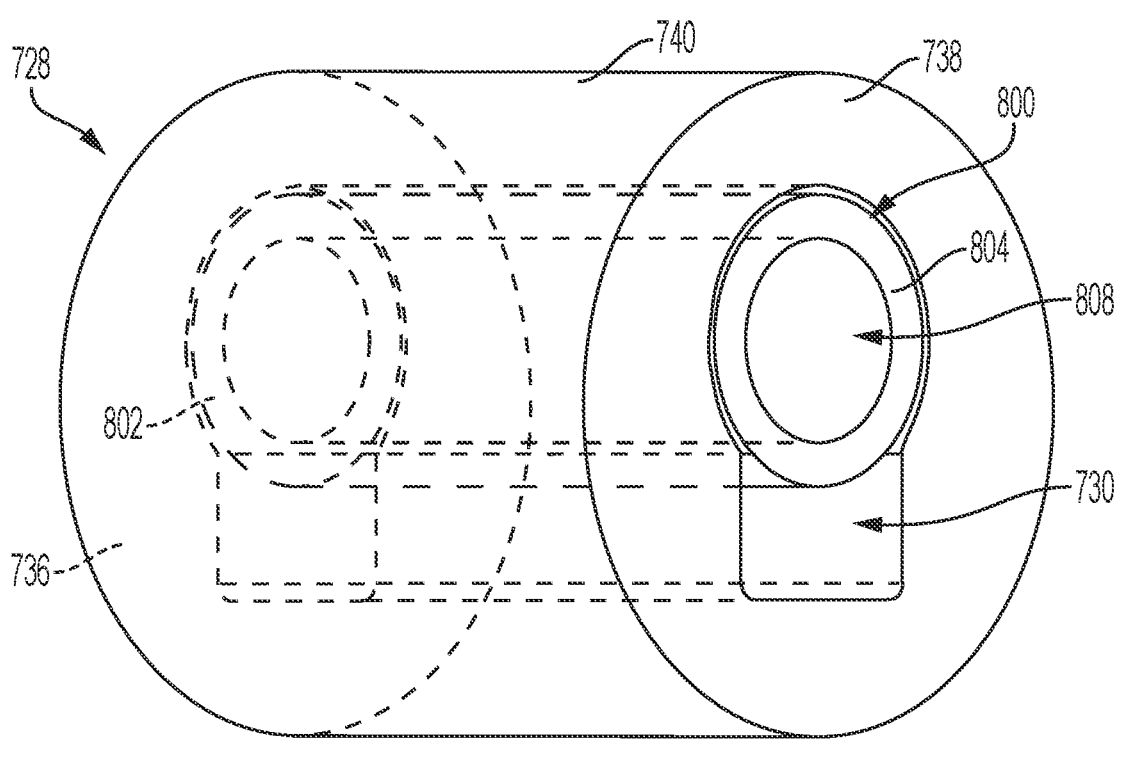
FIGS. 9A and 9B are isometric and end views, respectively, of the locking element of FIGS. 8A and 8B positioned within the joining element of FIGS. 7A and 7B in accordance with several embodiments of the present technology.
Figure 9B:
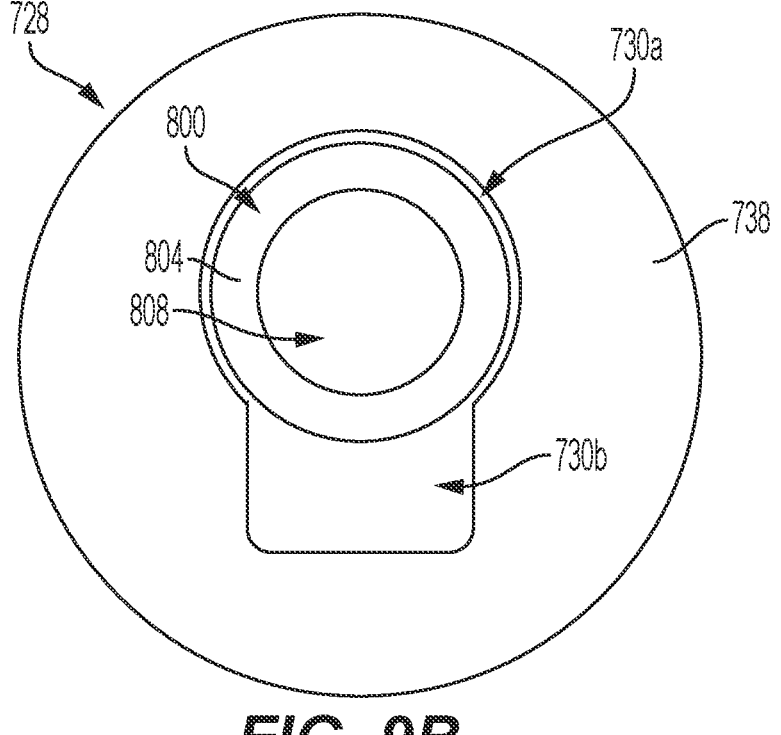

FIGS. 9A and 9B depict the locking element 800 assembled with the joining element 728. As shown in FIGS. 9A and 9B, the locking element 800 can be configured to be inserted into the aperture 730 of the joining element 728. The locking element 800 and the aperture 730 can be sized such that there is an interference fit, a transition fit, or a clearance fit (see FIGS. 9A and 9B) between the locking element 800 and the joining element 728. In some embodiments, the locking element 800 has a cross-sectional shape generally corresponding to a cross-sectional shape of at least a portion of the aperture 730 of the joining element 728. In some embodiments, the locking element 800 is configured to be positioned within the first portion 730*a* of the aperture 730 of the joining element 728 and the locking element 800 has a cross-sectional shape generally corresponding to the cross-sectional shape of the first portion 730*a* of the aperture 730 of the joining element 728. For example, as shown in FIGS. 9A and 9B, the locking element 800 can have a generally circular cross-sectional shape (e.g., the sidewall 806 is generally annular) corresponding to the generally circular cross-sectional shape of the first portion 730*a* of the aperture 730. The locking element 800 can be configured to be positioned within the aperture 730 such that the first end surface 802 of the locking element 800 is generally flush with the first end surface 736 of the joining element 728 and/or the second end surface 804 of the locking element 800 is generally flush with the second end surface 738 of the joining element 728. In some embodiments, a length of the locking element 800 is the same as a length of the joining element 728.

Figure 10A:
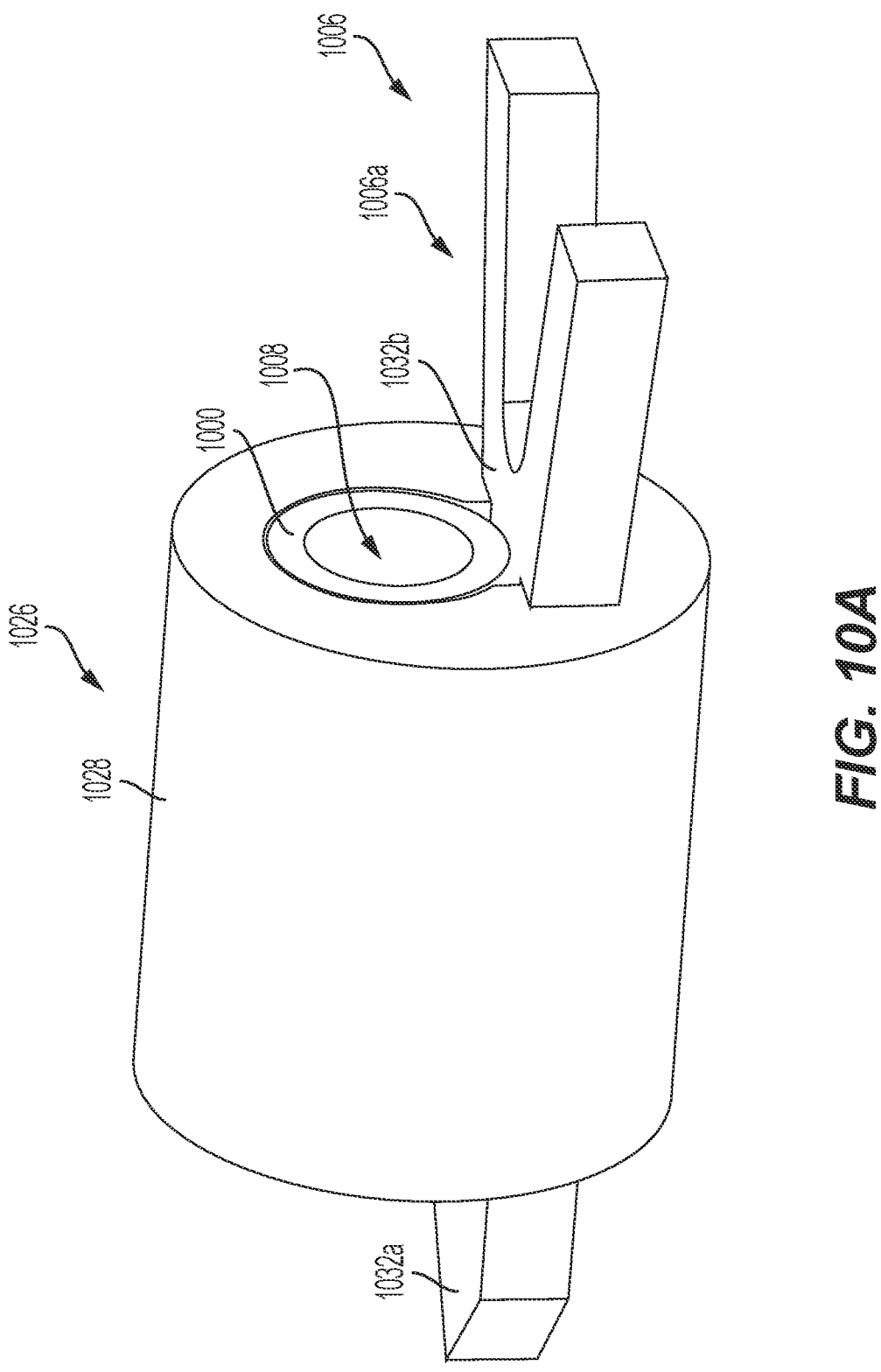
FIG. 10A is an isometric view of an attachment portion, an interventional element, and a locking element positioned within a joining element in accordance with several embodiments of the present technology.
Figure 10B:
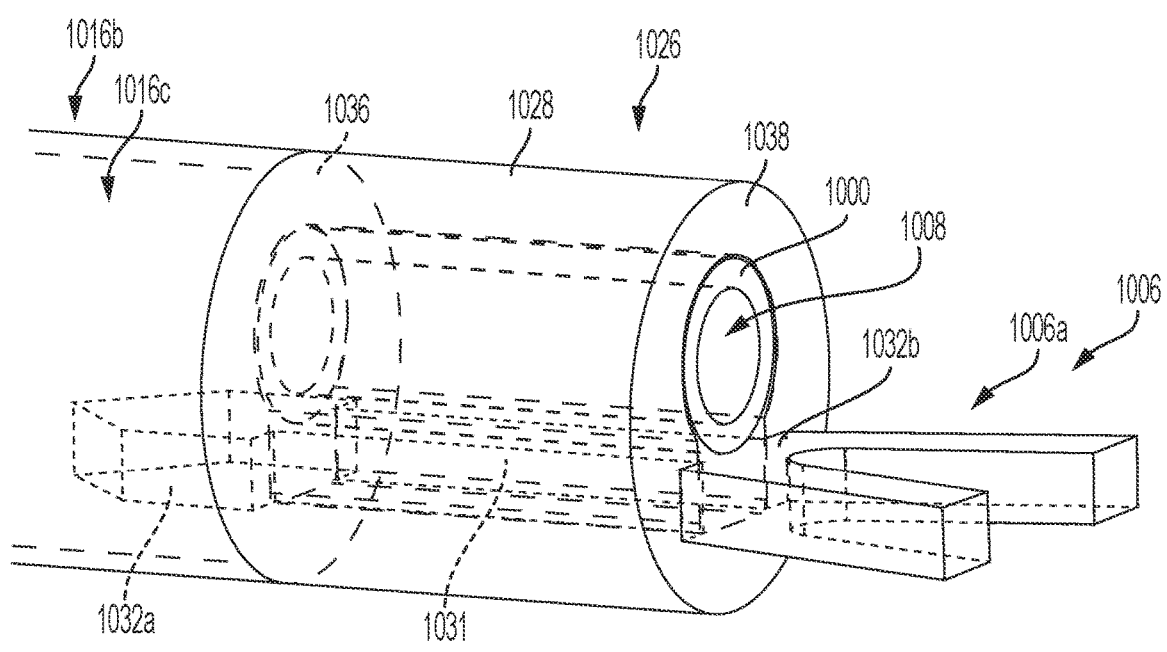
FIGS. 10B and 10C are isometric and cross-sectional views, respectively, of a connection between a manipulation member and the interventional element of FIG. 10A via the joining element and locking element of FIG. 10A in accordance with several embodiments of the present technology.
Figure 10C:
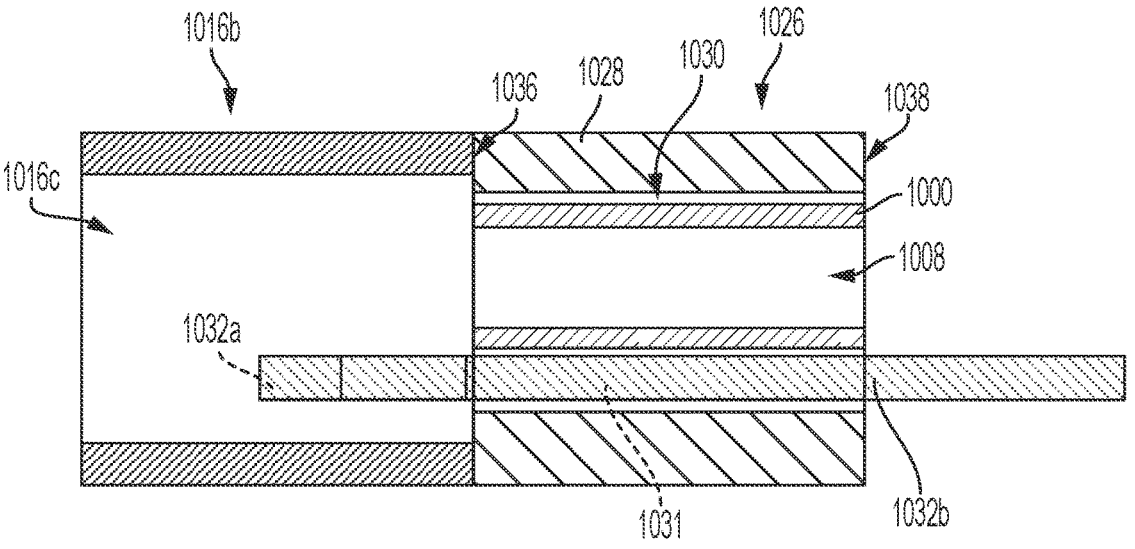
Figure 10D:
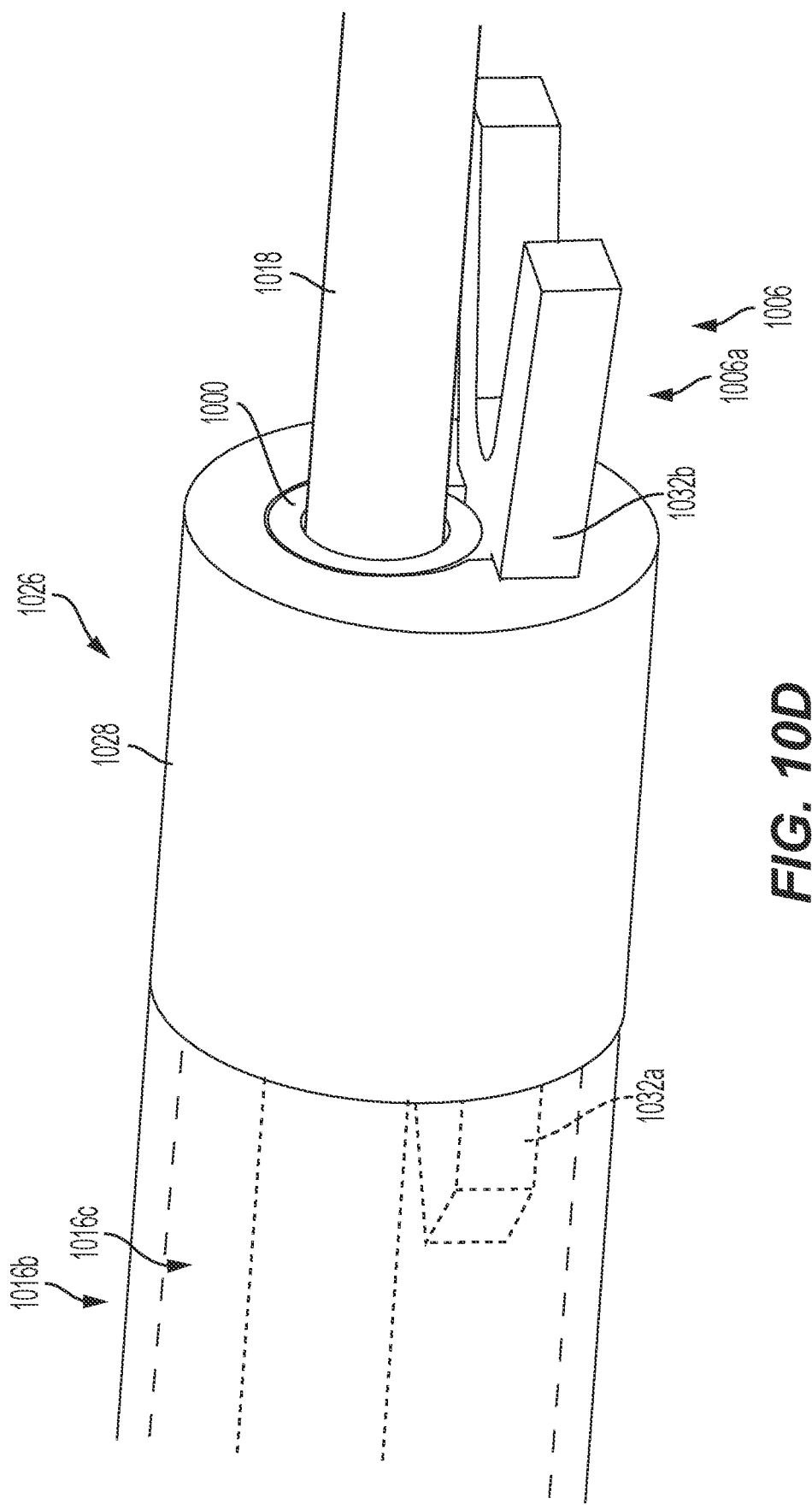
FIG. 10D is an isometric view of the interventional element and the locking element of FIGS. 10A-10C and a control member positioned within the joining element of FIGS. 10A-10C in accordance with several embodiments of the present technology.

FIG. 10A illustrates an interventional element 1006, a joining element 1028, and a locking element 1000 assembled in accordance with several embodiments of the present technology. FIGS. 10B and 10C illustrate a connection 1026 between a manipulation member 1016 and the assembled interventional element 1006, joining element 1028, and locking element 1000. FIG. 10D illustrates the connection 1026 with an elongate control member 1018 inserted through the locking element 1000. In some embodiments, the manipulation member 1016 can be similar to any of the embodiments of the manipulation member disclosed herein (e.g., manipulation member 116), except as further described, and the control member 1018 can be similar to any of the embodiments of the control member disclosed herein (e.g., control member 118), except as further described. The assembled interventional element 1006, joining element 1028, and locking element 1000 can be secured to a distal end portion 1016*b* of the manipulation member 1016. In some embodiments, the interventional element 1006 can be similar to any of the embodiments of the interventional element disclosed herein (e.g., interventional element 106), except as further described. For example, the interventional element 1006 can include an attachment portion 1006*a* comprising a retention region 1031, a proximal engagement feature 1032*a* and a distal engagement feature 1032*b*. In some embodiments, the joining element 1028 can be similar to any of the embodiments of the joining element disclosed herein (e.g., joining element 128, joining element 728, etc.). For example, the joining element 1028 can have an aperture 1030 extending therethrough. The aperture 1030 can have a first portion 1030*a* with a first cross-sectional shape and a second portion 1030*b* with a second cross-sectional shape. As described herein, the aperture 1030 can have a second dimension (e.g., second dimension d2) along a second direction (e.g., second direction A2) that is greater at the first portion 1030*a* of the aperture 1030 than the second dimension at the second portion 1030*b* of the aperture 1030. In some embodiments, the locking element 1000 can be similar to any of the embodiments of the locking element disclosed herein (e.g., locking element 800).

To secure the interventional element 1006 to the manipulation member 1016, the retention region 1031 of the attachment portion 1060*a* can be inserted into the aperture 1030 of the joining element 1028. As previously described with reference to FIGS. 4A and 4B, the retention region 1031 can have a greatest cross-sectional dimension that is no greater than a smallest cross-sectional dimension of the aperture 1030 of the joining element 1028. The proximal engagement feature 1032*a* and/or the distal engagement feature 1032*b* can have a greatest cross-sectional dimension that is less than the first cross-sectional dimension of the aperture 1030 along a first direction (e.g., first direction A1) and greater than the second cross-sectional dimension of the aperture along a second direction (e.g., second direction A2) in at least one location (e.g., at the second portion 1030*b* of the aperture 1030).

In some embodiments, the proximal engagement feature 1032*a* and the distal engagement feature 1032*b* each have a greatest cross-sectional dimension that is less than the second cross-sectional dimension at the first portion 1030*a* of the aperture 1030. In such embodiments, the attachment portion 1006*a* can be configured to be inserted into the first portion 1030*a* of the aperture 1030 when the attachment portion 1006*a* is positioned such that the greatest cross-sectional dimension of the proximal engagement feature 1032*a* and/or the distal engagement feature 1032*b* is generally aligned with the second cross-sectional dimension of the aperture 1030. The attachment portion 1006*a* may be slidably passed into the first portion 1030*a* of the aperture 1030 such that the retention region 1031 is positioned at least partially within the first portion 1030*a* of the aperture 1030 and the proximal engagement feature 1032*a* is positioned proximal of the joining element 1028. To mechanically interlock the attachment portion 1006*a* with the joining element 1028, the attachment portion 1006*a* can be radially displaced within the aperture 1030 until the retention region 1031 is positioned at least partially within the second portion 1030*b* of the aperture 1030. In such a configuration, the proximal engagement feature 1032*a* can engage a first end surface 1036 of the joining element 1028 and/or the distal engagement feature 1032*b* can engage a second end surface 1038 of the joining element 1028. Additionally or alternatively, the proximal engagement feature 1032*a* and/or the distal engagement feature 1032*b* may be configured to engage the aperture 1030 of the joining element 1028.

In some embodiments, the attachment portion 1006*a* can be positioned such that the greatest cross-sectional dimension of the proximal engagement feature 1032*a* and/or the distal engagement feature 1032*b* is generally aligned with the first (e.g., larger) cross-sectional dimension of the aperture 1030. In such an orientation relative to the aperture 1030, the attachment portion 1006*a* may be slidably passed into the aperture 1030 such that the retention region 1031 is positioned at least partially within the aperture 1030 and the proximal engagement feature 1032*a* is positioned proximal of the joining element 1028. As previously described with reference to FIGS. 4A-5B, the attachment portion 1006*a* can then be rotated in a circumferential direction approximately about the longitudinal axis of the joining element 1028 such that the greatest cross-sectional dimension of the proximal engagement feature 1032*a* and/or the distal engagement feature 1032*b* is aligned with the second (e.g., smaller) cross-sectional dimension of the aperture 1030. Additionally or alternatively, the attachment portion 1006*a* can be radially displaced within the aperture 1030 to position the attachment portion 1006*a* in a desired portion of the aperture 1030 (e.g., the second portion 1030*b* as described above).

The engagement features 1032*a*, 1032*b* can be configured to prevent and/or limit motion (e.g., longitudinal movement) of the interventional element 1006 relative to the joining element 1028 and thereby the manipulation member 1016. For example, as shown in FIGS. 10A-10C, the proximal engagement feature 1032*a* can be configured to abut the first end surface 1036 (i.e., the proximal-facing surface) of the joining element 1028 when the retention region 1031 is positioned within the aperture 1030 to prevent distal translation of the interventional element 1006 with respect to the joining element 1028. Similarly, the distal engagement feature 1032b can be configured to abut the second end surface 1038 (i.e., the distal-facing surface) of the joining element 1028 when the retention region 1031 is positioned within the aperture 1030 to prevent proximal translation of the interventional element 1006 with respect to the joining element 1028. Each of the engagement features 1032 can be configured to prevent distal translation, proximal translation, and/or rotation of the interventional element 1006 with respect to the joining element 1028. In addition to securing the interventional element 1006 to the manipulation member 1016, the mechanical interlock and contact between the attachment portion 1006a and the joining element 1028 can be configured to electrically couple the attachment portion 1006a to the joining element 1028 such that current supplied to the manipulation member 1016 may pass to the interventional element 1006 via the joining element 1028.

As shown in FIGS. 10A-10C, the locking element 1000 can be inserted into the aperture 1030 of the joining element 1028. For example, the locking element 1000 can be slidably inserted into the aperture 1030 of the joining element 1028. In some embodiments, the locking element 1000 is configured to be inserted into the aperture 1030 of the joining element 1028 after the attachment portion 1006a has been inserted into the aperture 1030 of the joining element 1028. The locking element 1000 can be inserted into the aperture 1030 of the joining element 1028 at a position that is radially adjacent to the attachment portion 1006a. For example, as shown in FIGS. 10A-10C, the locking element 1000 can be inserted into the first portion 1030a of the aperture 1030 of the joining element 1028 so that the locking element 1000 is radially adjacent to the attachment portion 1006a. As described herein with reference to FIGS. 8A and 8B, the locking element 1000 and the portion of the aperture 1030 of the joining element 1028 configured to receive the locking element 1000 can be sized so that there is an interference fit, a transition fit, or a clearance fit between the locking element 1000 and the joining element 1028. In various embodiments, the connection 1026 can comprise a bonding agent in addition or alternative to the joining element 1028, the locking element 1000, and/or a control member. The bonding agent can comprise adhesive, solder, welding flux, brazing filler, etc. In some embodiments, the bonding agent can bond to the connection 1026 without applying heat. For example, the bonding agent can comprise a UV-curable adhesive. In embodiments that comprise a polymer coating of the wire or employ polymer tubing as the locking element 1000, use of a bonding agent that avoids application of heat that would damage the polymer may be preferred.

The locking element 1000 can be configured to prevent and/or limit motion of the attachment portion 1006a with respect to the joining element 1028. In some embodiments, the locking element 1000 can be configured to prevent and/or limit radial translation and/or rotation of the attachment portion 1006a with respect to the joining element 1028. Such constraint of the attachment portion 1006a can prevent the attachment portion 1006a from reverting to a position and/or orientation in which the attachment portion 1006a can slidably pass through the aperture 1030 of the joining element 1028 and/or move proximally and/or distally relative to the joining element 1028.

In some embodiments, the joining element 1028 is configured to be secured to the manipulation member 1016 once the joining element 1028, the locking element 1000, and the interventional element 1006 have been assembled. As described herein, the joining element 1028 can be secured to the manipulation member 1016 via welding, adhesive, helical threaded engagement, interference fit or another suitable process. As the proximal engagement feature 1032a can be positioned proximal of the joining element 1028 in the assembled configuration, the proximal engagement feature 1032a can be positioned within a lumen 1016c of the manipulation member 1016 once the joining element 1028 is secured to the manipulation member 1016. The proximal engagement feature 1032a may be configured to avoid contact with a wall of the lumen 1016c of the manipulation member 1016 or to contact the wall of the lumen 1016c of the manipulation member 1016. In some embodiments, the joining element 1028 is configured to be secured to the manipulation member 1016 prior to assembly of the joining element 1028 with the locking element 1000 and/or the interventional element 1006.

In some embodiments, for example as shown in FIG. 10D, the control member 1018 can be inserted through the aperture 1008 of the locking element 1000. The elongate control member 1018 can be slidably inserted through the aperture 1008 of the locking element 1000. As noted previously, in some embodiments the control member 1018 can also serve as a negative (e.g., return) electrode, or as a second electrode, for example taking the form of an elongated wire that is insulated along at least a portion of its length, with one or more exposed portions of the wire that are configured to electrically contact electrolytic media, such as blood, thrombus, saline, etc. while positioned at the treatment site. In such embodiments the interventional element 1006 can take the form of a positive (e.g., delivery) electrode, or as a first electrode, with one or more exposed portions that are configured to electrically contact electrolytic media such as thrombus, blood, saline, etc.

In some embodiments, a bonding agent (e.g., weld, adhesive, solder, etc.) can be applied to some or all of the control member 1018, the locking element 1000, the joining element 1028, and/or the attachment portion 1006a before, during, or after assembly of the connection 1026. In some embodiments, the control member 1018 may be omitted from the aperture 1008 of the locking element 1000, and a filler material such as solder, adhesive, epoxy, etc., or some other element, may be placed in the aperture 1008.

CONCLUSION

Although many of the embodiments are described above with respect to systems, devices, and methods for electrically enhanced retrieval of material from vessel lumens, the technology is applicable to other applications and/or other approaches, such as mechanical thrombectomy. Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above with reference to FIGS. 1A-10D.

The descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

The invention claimed is:

1. A medical device comprising:
a manipulation assembly having a distal portion configured to be intravascularly positioned within a blood vessel lumen, the manipulation assembly comprising:
an elongate tubular member, the tubular member having a proximal portion, a distal portion, and a lumen extending therein; and
a joining element located at the distal portion of the elongate tubular member, the joining element having a proximal-facing surface, a distal-facing surface opposite the proximal-facing surface, and a lumen extending from the proximal-facing surface to the distal-facing surface of the joining element, wherein the lumen of the joining element has a lumen greatest cross-sectional dimension and a lumen smallest cross-sectional dimension;
a control member positioned within the lumen of the joining element, and
an interventional element comprising a proximally located attachment portion having a distal engagement feature, a proximal engagement feature, and a retention region therebetween, wherein the distal and proximal engagement features each protrude outwardly with respect to the retention region,
wherein the proximal engagement feature has an engagement feature greatest cross- sectional dimension and an engagement feature smallest cross-sectional dimension, the engagement feature greatest cross-sectional dimension being greater than the lumen smallest cross-sectional dimension and less than the lumen greatest cross-sectional dimension,
wherein the retention region is positioned within the lumen of the joining element such that the distal engagement feature is configured to limit proximal translation of the interventional element relative to the joining element and the proximal engagement feature is configured to limit distal translation of the interventional element relative to the joining element, and
wherein the control member is positioned adjacent to the retention region of the attachment portion such that the control member is configured to limit radial translation of the rentention region within the lumen of the joining element.

2. The medical device of claim 1, wherein the lumen of the joining element includes a first portion having a first cross-sectional shape and a second portion having a second cross-sectional shape, and wherein the second portion is radially adjacent to the first portion.

3. The medical device of claim 2, further comprising a locking element having a cross-sectional shape corresponding, at least in part, to the first cross-sectional shape of the first portion of the lumen of the joining element.

4. The medical device of claim 3, wherein the retention region is positioned within the second portion of the lumen of the joining element and the locking element is positioned within the first portion of the lumen of the joining element such that the locking element is also configured to limit radial translation of the retention region within the lumen of the joining element.

5. The medical device of claim 3, wherein the elongate tubular member is configured to be coupled to a first terminal of an extracorporeal power supply, wherein the control member extends through the lumen of the tubular member and through a lumen of the locking element and wherein the control member is configured to be coupled to a second terminal of the extracorporeal power supply.

6. The medical device of claim 1, further comprising a first electrode formed by or coupled to the interventional element and a second electrode formed by or coupled to the control member.

7. The medical device of claim 6, wherein the first and second electrodes each comprise a surface formed of gold.

8. The medical device of claim 6, wherein the first and second electrodes are configured to be of opposite polarities.

9. The medical device of claim 5, wherein the control member provides a first current path through the lumen of the locking element which is insulated from a second current path conducted by the joining element to the interventional element.

10. The medical device of claim 1, wherein a filler material is disposed within the lumen of the joining element.

11. The medical device of claim 2, wherein the first cross-sectional shape is generally circular and the second cross-sectional shape is generally rectangular.

12. The medical device of claim 1, wherein the proximal engagement feature has a first width, the distal engagement feature of the attachment portion has a second width, and the retention region of the attachment portion has a third width less than the first width and the second width.

13. The medical device of claim 1, wherein the distal engagement feature abuts the distal-facing surface of the joining element and the proximal engagement feature abuts the proximal-facing surface of the joining element.

14. The medical device of claim 2, wherein the interventional element is configured to be coupled to the manipulation assembly by positioning the retention region of the attachment portion of the interventional element within the first portion of the lumen of the joining element and radially displacing the retention region into the second portion of the lumen of the joining element.

15. A medical device comprising:

a manipulation assembly having a distal portion configured to be intravascularly positioned within a blood vessel lumen, the manipulation assembly comprising:

a hypotube configured to be coupled to a first electrical terminal, the hypotube having a proximal portion, a distal portion, and a lumen extending therein;

a joining element located at the distal portion of the hypotube, the joining element comprising a first end surface, a second end surface opposite the first end surface along a length of the joining element, an annular sidewall therebetween, and a lumen extending from the first end surface to the second end surface of the joining element, wherein the lumen of the joining element has a lumen greatest cross-sectional dimension and a lumen smallest cross-sectional dimension;

an elongate member configure to be coupled to a second electrical terminal, the elongate member extending through the lumen of the joining element:

an insulating layer dispos between at le st a portion of the hypotube and at least a portion of the elongate member, and an interventional element comprising an attachment portion comprising a projection including a flange extending laterally away from a longitudinal axis of the device, wherein the flange has a flange greatest cross-sectional dimension and a flange smallest cross-sectional dimension, the flange greatest cross-sectional dimension being greater than the lumen smallest cross-sectional dimension and less than the lumen greatest cross-sectional dimension, and the flange smallest cross-sectional dimension being less than the lumen smallest cross- sectional dimension, wherein the projection is positioned within the lumen of the joining element such that the flange engages the joining element and limits longitudinal movement of the interventional element with respect to the joining element, and wherein the elongate member is positioned adjacent to the projection such that the elongate member is configured to limit radial translation of the projection within the lumen of the joining element.

16. The medical device of claim 15, further comprising a tubular element positioned within the lumen of the joining element.

17. The medical device of claim 16, wherein the projection is positioned within the lumen of the joining element at a position radially adjacent to the tubular element such that the tubular element also limits radial movement of the interventional element with respect to the joining element.

18. The medical device of claim 15, wherein the flange is a first flange, wherein the projection includes a second flange extending laterally away from the longitudinal axis of the device, and wherein the first flange is configured to engage the first end surface of the joining element to limit distal movement of the interventional element with respect to the joining element and the second flange is configured to engage the second end surface of the joining element to limit proximal movement of the interventional element with respect to the joining element.

19. The medical device of claim 16, wherein the tubular element is secured within the lumen of the joining element via an interference fit or a transition fit.

20. A medical device comprising:

a manipulation assembly having a distal portion configured to be intravascularly positioned within a blood vessel lumen, the manipulation assembly comprising:

a tubular member configured to be coupled to a first electrical terminal, the tubular member having a proximal portion, a distal portion, and a lumen extending therein, wherein the distal portion of the tubular member comprises an aperture;

an elongate member configured to be coupled to a second electrical terminal, the elongate member extending through the lumen of the tubular member; and an insulating layer disposed between at least a portion of the tubular member and at least a portion of the elongate member; and an interventional element having a proximally located attachment portion, wherein the attachment portion includes a proximal engagement portion that is slidably received within the aperture of the distal portion of the tubular member such that the attachment portion engages the tubular member, and wherein the proximal engagement portion is entirely disposed within the lumen of the tubular member, wherein the elongate member is positioned adjacent to the attachment portion such that the elongate member is configured to limit radial translation of the attachment portion within the lumen of the tubular member.

21. The medical device of claim 20, wherein the aperture comprises a first portion with a generally circular cross-sectional shape and a second portion with a generally rectangular cross-sectional shape.

22. The medical device of claim 21, further comprising a locking element having a lumen extending therethrough.

23. The medical device of claim 22, wherein the attachment portion is slidably received within the second portion of the aperture of the distal portion of the tubular member, and wherein when the attachment portion is positioned within the second portion of the aperture and the locking element is positioned within the first portion of the aperture, the attachment portion engages the tubular member and the locking element engages the tubular member and the attachment portion.

24. The medical device of claim 23, wherein the locking element is also configured to limit rotation and radial displacement of the attachment portion within the aperture of the tubular member.

25. The medical device of claim 20, wherein the attachment portion of the interventional element comprises an arm and a protrusion thereon, and wherein the arm is configured to be positioned within the aperture and the protrusion is configured to engage the tubular member.

* * * * *